(12) United States Patent
Inoue et al.

(10) Patent No.: US 8,399,665 B2
(45) Date of Patent: Mar. 19, 2013

(54) ORGANOMETALLIC COMPLEX, AND LIGHT-EMITTING ELEMENT, LIGHT-EMITTING DEVICE, ELECTRONIC DEVICE AND ELECTRONIC DEVICE USING THE ORGANOMETALLIC COMPLEX

(75) Inventors: Hideko Inoue, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 165 days.

(21) Appl. No.: 12/898,377

(22) Filed: Oct. 5, 2010

(65) Prior Publication Data

US 2011/0082296 A1 Apr. 7, 2011

(30) Foreign Application Priority Data

Oct. 7, 2009 (JP) .................................. 2009-232961

(51) Int. Cl.
*C07F 15/00* (2006.01)
(52) U.S. Cl. ..................................................... 544/225
(58) Field of Classification Search .................... 544/225
See application file for complete search history.

(56) References Cited

U.S. PATENT DOCUMENTS

| 2005/0221123 | A1 | 10/2005 | Inoue et al. |
| 2006/0263636 | A1 | 11/2006 | Ohsawa et al. |
| 2007/0129545 | A1 | 6/2007 | Inoue et al. |
| 2007/0244320 | A1 | 10/2007 | Inoue et al. |
| 2008/0122350 | A1 | 5/2008 | Sakata et al. |
| 2008/0149923 | A1 | 6/2008 | Ohsawa et al. |
| 2008/0233432 | A1 | 9/2008 | Inoue et al. |
| 2009/0015143 | A1 | 1/2009 | Inoue et al. |
| 2010/0105902 | A1 | 4/2010 | Inoue et al. |

OTHER PUBLICATIONS

Inoue, H. et al, "A Reaction of Singlet Oxygen with an Unsaturated Organic Molecule, 6.1.4, Quencher and Photosensitizer," *Basic Chemistry Course Photochemistry I*, Maruzen Co., Ltd., Sep. 30, 1999, pp. 106-110 (with English abstract).

Zhang, G-L et al, "Synthesis and Luminescence Property of a New Yellow Phosphorescent Iridium(III) Pyrazine Complex," Chemical Journal of Chinese Universities, vol. 25, No. 3, Mar. 1, 2004, pp. 397-400 (with English abstract).

Zhang et al., "Synthesis and Luminescence Property of a New Yellow Phosphorescent Iridium(III) Pyrazine Complex", Chemical Journal of Chinese Universities, Mar. 1, 2004, vol. 25, No. 3, pp. 397-400 (English translation).

*Primary Examiner* — Brian McDowell
(74) *Attorney, Agent, or Firm* — Husch Blackwell LLP

(57) ABSTRACT

An object is to provide a novel organometallic complex capable of emitting phosphorescence, an organometallic complex which exhibits deep red emission, and a light-emitting element which provides deep red emission. Provided is an organometallic complex having a structure represented by the following General Formula (G1).

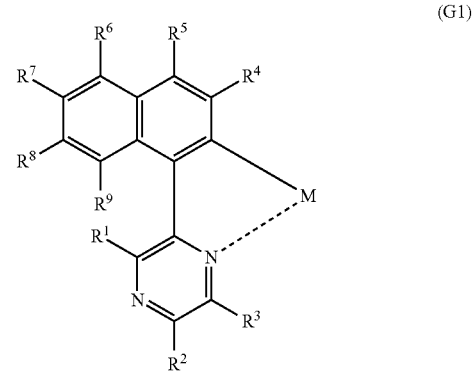

(G1)

In the formula, $R^1$, $R^2$, $R^3$, $R^4$, $R^5$, $R^6$, $R^7$, $R^8$, and $R^9$ represent substituents, and M is a central metal and represents either a Group 9 element or a Group 10 element.

24 Claims, 13 Drawing Sheets

ORGANOMETALLIC COMPLEX, AND LIGHT-EMITTING ELEMENT, LIGHT-EMITTING DEVICE, ELECTRONIC DEVICE AND ELECTRONIC DEVICE USING THE ORGANOMETALLIC COMPLEX

BACKGROUND OF THE INVENTION

1. Field of the Invention

The present invention relates to an organometallic complex. In particular, the present invention relates to an organometallic complex that is capable of converting a triplet excited state into luminescence.

2. Description of the Related Art

Organic compounds are brought into an excited state by absorption of light. Through this excited state, various reactions (photochemical reactions) are caused in some cases, or luminescence is generated in some cases. Therefore, the organic compounds have a wide range of applications.

As one example of the photochemical reactions, a reaction of singlet oxygen with an unsaturated organic molecule (oxygen addition) is known (see Non-patent Document 1, for example). Since the ground state of oxygen molecules is a triplet state, oxygen molecules do not form a singlet state (singlet oxygen) when they are excited directly by light. In contrast, when oxygen molecules interact with triplet excited molecules other than oxygen, the oxygen molecules form singlet oxygen, thereby leading to an oxygen addition reaction. Here, the compound that forms the triplet excited molecules by light and enables formation of singlet oxygen is called a photo sensitizer.

Thus, formation of singlet oxygen requires a photosensitizer that can form triplet excited molecules by light. However, since the ground state of an ordinary organic compound is a singlet state, formation of a triplet excited state by light is forbidden transition; thus, triplet excited molecules are difficult to generate. Therefore, as the photosensitizer, it is necessary to use a compound that can easily cause intersystem crossing from the singlet excited state to the triplet excited state (or a compound that allows the forbidden transition through excitation directly by light into the triplet excited state). In other words, such a compound can be used as the photosensitizer and is useful.

Further, such a compound often exhibits phosphorescence. Phosphorescence refers to luminescence generated by transition between different energies in multiplicity. In an ordinary organic compound, phosphorescence refers to luminescence generated in returning from the triplet excited state to the singlet ground state (in contrast, fluorescence refers to luminescence in returning from the singlet excited state to the singlet ground state). Application fields of a compound capable of exhibiting phosphorescence, that is, a compound capable of converting the triplet excited state into luminescence (hereinafter, referred to as a phosphorescent compound), include a light-emitting element including an organic compound as a light-emitting substance.

An example of the structure of such a light-emitting element is a simple one in which a light-emitting layer containing an organic compound that is a light-emitting substance is merely provided between electrodes. Light-emitting elements having such a structure can achieve thinness, light-weight, high-speed response to signals, low-voltage DC drive, and the like. Therefore, attention has been directed to the light-emitting elements as next-generation flat panel display elements. Further, displays using such light-emitting elements are superior in contrast, image quality, and wide viewing angle.

The light-emitting element including an organic compound as a light-emitting substance has a light emission mechanism of a carrier injection type: a voltage is applied between electrodes where a light-emitting layer is interposed, electrons and holes injected from the electrodes recombine to make the light-emitting substance excited, and then light is emitted in returning from the excited state to the ground state. As in the case of excitation described above, types of excited state include a singlet excited state (S*) and a triplet excited state (T*). The statistical generation ratio thereof in light-emitting elements is considered to be S*:T*=1:3.

At room temperature, a compound capable of converting a singlet excited state to luminescence (hereinafter, referred to as a fluorescent compound) exhibits only luminescence from the singlet excited state (fluorescence), not luminescence from the triplet excited state (phosphorescence). Therefore, the internal quantum efficiency (the ratio of generated photons to injected carriers) of a light-emitting element including a fluorescent compound is assumed to have a theoretical limit of 25%, on the basis of S*:T*=1:3.

On the other hand, in the case of a light-emitting element including a phosphorescent compound described above, the internal quantum efficiency thereof can be improved to 75% to 100% in theory; i.e., the emission efficiency thereof can be 3 to 4 times as much as that of a light-emitting element including a fluorescent compound. Therefore, light-emitting elements including a phosphorescent compound have been actively developed in recent years in order to achieve highly-efficient light-emitting elements (e.g., see Non-Patent Document 2). Organometallic complexes that contain iridium or the like as a central metal have particularly attracted attention as phosphorescent compounds because of their high phosphorescence quantum yield.

REFERENCES

Non-Patent Documents

[Non-Patent Document 1] Inoue, Haruo et al., *Basic Chemistry Course PHOTOCHEMISTRY I*, pp. 106-110, Maruzen Co., Ltd.

[Non-Patent Document 2] Zhang, Guo-Lin and five others (2004) *Gaodeng Xuexiao Huaxue Xuebao*, vol. 25, No. 3, pp. 397-400.

SUMMARY OF THE INVENTION

An object of one embodiment of the present invention is to provide a novel organometallic complex capable of emitting phosphorescence by using an organic compound, with which a variety of derivatives can be easily synthesized, as a ligand. Another object of one embodiment of the present invention is to provide an organometallic complex that exhibits deep red emission.

One embodiment of the present invention is an organometallic complex formed by ortho-metalation of an α-naphthylpyrazine derivative, which is represented by General Formula (G0) below, with an ion of a metal belonging to Group 9 or Group 10. Another embodiment of the present invention is an organometallic complex exhibiting deep red phosphorescence, which is formed by ortho-metalation of an α-naphthylpyrazine derivative represented by General Formula (G0) below with an ion of a metal belonging to Group 9 or Group 10.

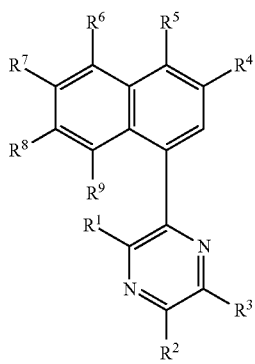

(G0)

Therefore, a structure of the present invention is an organometallic complex having a structure represented by General Formula (G1) below.

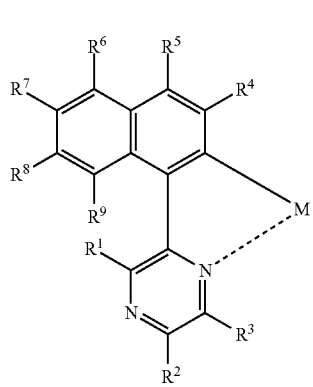

(G1)

In the formula, $R^1$ and $R^2$ individually represent any of an alkyl group having 1 to 4 carbon atoms, an alkoxy group having 1 to 4 carbon atoms, an alkylthio group having 1 to 4 carbon atoms, or an alkoxycarbonyl group having 1 to 5 carbon atoms. $R^3$ represents hydrogen or an alkyl group having 1 to 4 carbon atoms. In addition, $R^4, R^5, R^6, R^7, R^8$, and $R^9$ individually represent any of hydrogen, an alkyl group having 1 to 4 carbon atoms, an alkoxy group having 1 to 4 carbon atoms, a halogen group, a haloalkyl group having 1 to 4 carbon atoms, or an aryl group having 6 to 13 carbon atoms. A pair of adjacent substituents selected from the substituents $R^4, R^5, R^6, R^7, R^8$, and $R^9$ may be bonded to each other to form a saturated ring structure. M is a central metal and represents either a Group 9 element or a Group 10 element.

Examples of the substituents represented as $R^1$ to $R^9$ in the above General Formula (G1) include: a methyl group, an ethyl group, a propyl group, an isopropyl group, a butyl group, a sec-butyl group, an isobutyl group, a tert-butyl group, and the like, as the alkyl group having 1 to 4 carbon atoms; a methoxy group, an ethoxy group, a propoxy group, an isopropoxy group, a butoxy group, a sec-butoxy group, an isobutoxy group, a tert-butoxy group, and the like, as the alkoxy group having 1 to 4 carbon atoms; a methylthio group, an ethylthio group, a propylthio group, an isopropylthio group, a butylthio group, a sec-butylthio group, an isobutylthio group, a tert-butylthio group, and the like, as the alkylthio group having 1 to 4 carbon atoms; a methoxycarbonyl group, an ethoxycarbonyl group, a propoxycarbonyl group, an isopropoxy carbonyl group, a butoxycarbonyl group, a sec-butoxycarbonyl group, an isobutoxycarbonyl group, a tert-butoxycarbonyl group, and the like, as the alkoxycarbonyl group having 1 to 5 carbon atoms; a fluoro group, a chloro group, a bromo group, an iodine group, and the like, as the halogen group; a fluoromethyl group, a difluoromethyl group, a trifluoromethyl group, a chloromethyl group, a dichloromethyl group, a bromomethyl group, a 2,2,2-trifluoroethyl group, a 3,3,3-trifluoropropyl group, and the like, as the a haloalkyl group having 1 to 4 carbon atoms; a phenyl group, a tolyl group, a biphenylyl group, a fluorenyl group, a 1-naphthyl group, a 2-naphthyl group as the aryl group having 6 to 13 carbon atoms; and the like.

In General Formula (G1) above, $R^3$ is preferably hydrogen or alternatively both $R^3$ and $R^9$ are preferably hydrogen in terms of synthesis yield, because such structures reduce hindrance of a pyrazine derivative. Thus, a more preferred embodiment is an organometallic complex having a structure represented by General Formula (G2) below.

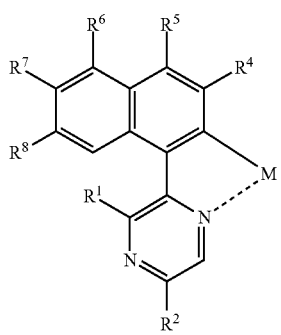

(G2)

In the formula, $R^1$ and $R^2$ individually represent any of an alkyl group having 1 to 4 carbon atoms, an alkoxy group having 1 to 4 carbon atoms, an alkylthio group having 1 to 4 carbon atoms, or an alkoxycarbonyl group having 1 to 5 carbon atoms. In addition, $R^4, R^5, R^6, R^7$, and $R^8$ individually represent any of hydrogen, an alkyl group having 1 to 4 carbon atoms, an alkoxy group having 1 to 4 carbon atoms, a halogen group, a haloalkyl group having 1 to 4 carbon atoms, or an aryl group having 6 to 13 carbon atoms. A pair of adjacent substituents selected from the substituents $R^4, R^5, R^6, R^7$, and $R^8$ may be bonded to each other to form a saturated ring structure. M is a central metal and represents either a Group 9 element or a Group 10 element.

In the above General Formula (G2), $R^4, R^6, R^7$, and $R^8$ are preferably hydrogen for ease of synthesis. Thus, a more preferable structure of the present invention is an organometallic complex having a structure represented by General Formula (G3) below.

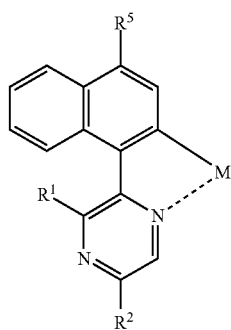

(G3)

In the formula, $R^1$ and $R^2$ individually represent any of an alkyl group having 1 to 4 carbon atoms, an alkoxy group having 1 to 4 carbon atoms, an alkylthio group having 1 to 4 carbon atoms, or an alkoxycarbonyl group having 1 to 5 carbon atoms. In addition, $R^5$ represents any of hydrogen, an alkyl group having 1 to 4 carbon atoms, an alkoxy group having 1 to 4 carbon atoms, a halogen group, a haloalkyl group having 1 to 4 carbon atoms, or an aryl group having 6 to 13 carbon atoms. M is a central metal and represents either a Group 9 element or a Group 10 element.

Here, specifically, the organometallic complex having the structure represented by General Formula (G1) above is preferably an organometallic complex represented by General Formula (G4) below, because of its easy synthesis.

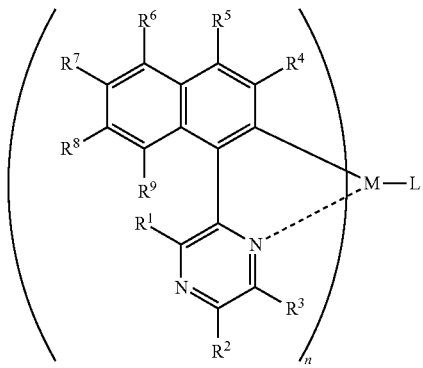

(G4)

In the formula, $R^1$ and $R^2$ individually represent any of an alkyl group having 1 to 4 carbon atoms, an alkoxy group having 1 to 4 carbon atoms, an alkylthio group having 1 to 4 carbon atoms, or an alkoxycarbonyl group having 1 to 5 carbon atoms. $R^3$ represents hydrogen or an alkyl group having 1 to 4 carbon atoms. In addition, $R^4$, $R^5$, $R^6$, $R^7$, $R^8$, and $R^9$ individually represent any of hydrogen, an alkyl group having 1 to 4 carbon atoms, an alkoxy group having 1 to 4 carbon atoms, a halogen group, a haloalkyl group having 1 to 4 carbon atoms, or an aryl group having 6 to 13 carbon atoms. A pair of adjacent substituents selected from the substituents $R^4$, $R^5$, $R^6$, $R^7$, $R^8$, and $R^9$ may be bonded to each other to form a saturated ring structure. M is a central metal and represents either a Group 9 element or a Group 10 element. L represents a monoanionic ligand. Moreover, n is 2 when M is a Group 9 element or n is 1 when M is a Group 10 element.

Here, specifically, the organometallic complex having the structure represented by General Formula (G2) above is preferably an organometallic complex represented by General Formula (G5) below, because of its easy synthesis.

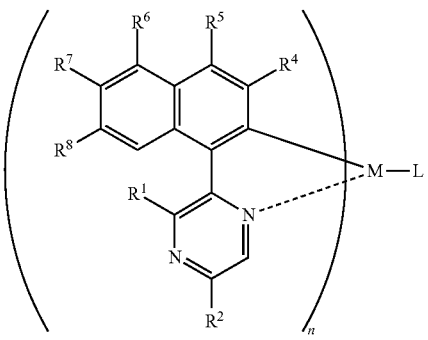

(G5)

In the formula, $R^1$ and $R^2$ individually represent any of an alkyl group having 1 to 4 carbon atoms, an alkoxy group having 1 to 4 carbon atoms, an allylthio group having 1 to 4 carbon atoms, or an alkoxycarbonyl group having 1 to 5 carbon atoms. In addition, $R^4$, $R^5$, $R^6$, $R^7$, and $R^8$ individually represent any of hydrogen, an alkyl group having 1 to 4 carbon atoms, an alkoxy group having 1 to 4 carbon atoms, a halogen group, a haloalkyl group having 1 to 4 carbon atoms, or an aryl group having 6 to 13 carbon atoms. A pair of adjacent substituents selected from the substituents $R^4$, $R^5$, $R^6$, $R^7$, and $R^8$ may be bonded to each other to form a saturated ring structure. M is a central metal and represents either a Group 9 element or a Group 10 element. L represents a monoanionic ligand. Moreover, n is 2 when M is a Group 9 element or n is 1 when M is a Group 10 element.

Specifically, the organometallic complex having the structure represented by General Formula (G3) above is preferably an organometallic complex represented by General Formula (G6) below, because of its easy synthesis.

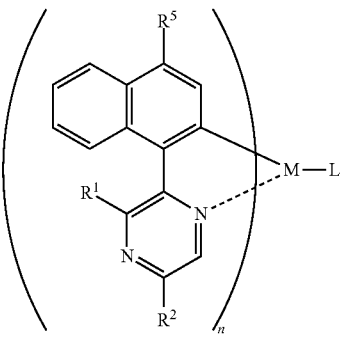

(G6)

In the formula, $R^1$ and $R^2$ individually represent any of an alkyl group having 1 to 4 carbon atoms, an alkoxy group having 1 to 4 carbon atoms, an alkylthio group having 1 to 4 carbon atoms, or an alkoxycarbonyl group having 1 to 5 carbon atoms. In addition, $R^5$ represents any of hydrogen, an alkyl group having 1 to 4 carbon atoms, an alkoxy group having 1 to 4 carbon atoms, a halogen group, a haloalkyl group having 1 to 4 carbon atoms, or an aryl group having 6 to 13 carbon atoms. M is a central metal and represents either a Group 9 element or a Group 10 element. L represents a monoanionic ligand. Moreover, n is 2 when M is a Group 9 element or n is 1 when M is a Group 10 element.

The above-described monoanionic ligand L is preferably any of a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen. More preferably, the monoanionic ligand L is a monoanionic ligand represented by Structural Formulas (L1) to (L6) below. Since these ligands have high coordinative ability and can be obtained at low price, they are useful.

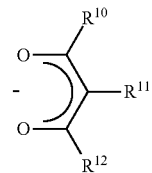

(L1)

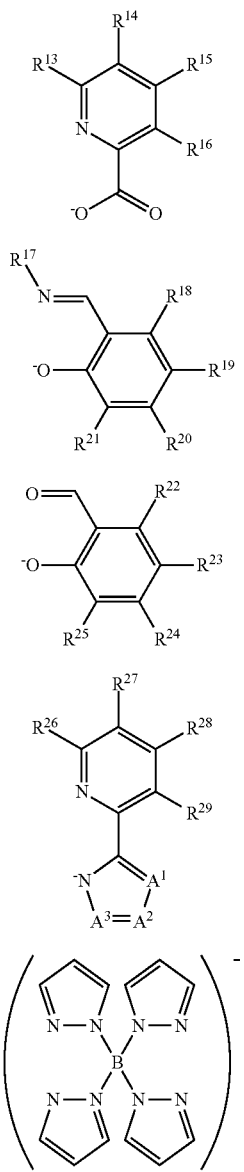

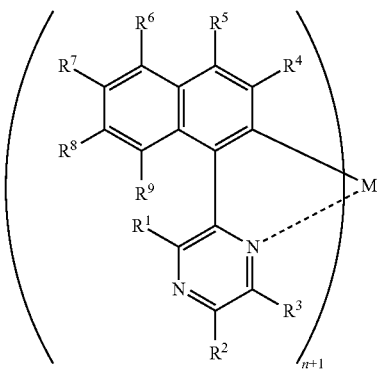

In the formula, $R^1$ and $R^2$ individually represent any of an alkyl group having 1 to 4 carbon atoms, an alkoxy group having 1 to 4 carbon atoms, an alkylthio group having 1 to 4 carbon atoms, or an alkoxycarbonyl group having 1 to 5 carbon atoms. $R^3$ represents hydrogen or an alkyl group having 1 to 4 carbon atoms. In addition, $R^4$, $R^5$, $R^6$, $R^7$, $R^8$, and $R^9$ individually represent any of hydrogen, an alkyl group having 1 to 4 carbon atoms, an alkoxy group having 1 to 4 carbon atoms, a halogen group, a haloalkyl group having 1 to 4 carbon atoms, or an aryl group having 6 to 12 carbon atoms. A pair of adjacent substituents selected from the substituents $R^4$, $R^5$, $R^6$, $R^7$, $R^8$, and $R^9$ may be bonded to each other to form a saturated ring structure. M is a central metal and represents either a Group 9 element or a Group 10 element. Moreover, n is 2 when M is a Group 9 element or n is 1 when M is a Group 10 element.

Specifically, the organometallic complex having the structure represented by General Formula (G2) above is preferably an organometallic complex represented by General Formula (G8) below, because of its easy synthesis.

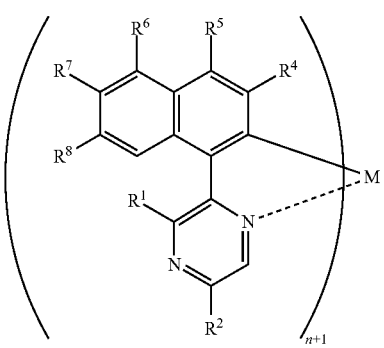

In the formula, $R^{10}$ to $R^{29}$ individually represent any of hydrogen, an alkyl group having 1 to 4 carbon atoms, a halogen group, a haloalkyl group having 1 to 4 carbon atoms, an alkoxy group having 1 to 4 carbon atoms, or an alkylthio group having 1 to 4 carbon atoms. In addition, $A^1$, $A^2$, and $A^3$ individually represent nitrogen N or carbon C—R, and R represents hydrogen, an alkyl group having 1 to 4 carbon atoms, a halogen group, or a haloalkyl group having 1 to 4 carbon atoms.

For more efficient emission of phosphorescence, a heavy metal is preferable as a central metal in terms of a heavy atom effect. Therefore, one feature of the present invention is that iridium or platinum is employed as the central metal M in each of the above organometallic complexes of the present invention.

Specifically, the organometallic complex having the structure represented by General Formula (G1) above is preferably an organometallic complex represented by General Formula (G7) below, because of its easy synthesis.

In the formula, $R^1$ and $R^2$ individually represent any of an alkyl group having 1 to 4 carbon atoms, an alkoxy group having 1 to 4 carbon atoms, an alkylthio group having 1 to 4 carbon atoms, or an alkoxycarbonyl group having 1 to 5 carbon atoms. In addition, $R^4$, $R^5$, $R^6$, $R^7$, and $R^8$ individually represent any of hydrogen, an alkyl group having 1 to 4 carbon atoms, an alkoxy group having 1 to 4 carbon atoms, a halogen group, a haloalkyl group having 1 to 4 carbon atoms, or an aryl group having 6 to 12 carbon atoms. A pair of adjacent substituents selected from the substituents $R^4$, $R^5$, $R^6$, $R^7$, and $R^8$ may be bonded to each other to form a saturated ring structure. M is a central metal and represents either a Group 9 element or a Group 10 element. Moreover, n is 2 when M is a Group 9 element or n is 1 when M is a Group 10 element.

Specifically, the organometallic complex having the structure represented by General Formula (G3) above is preferably an organometallic complex represented by General Formula (G9) below, because of its easy synthesis.

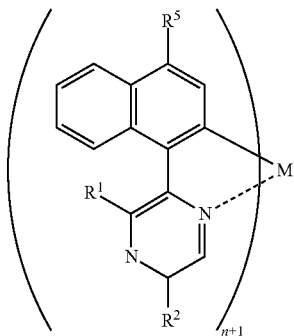

(G9)

In the formula, $R^1$ and $R^2$ individually represent any of an alkyl group having 1 to 4 carbon atoms, an alkoxy group having 1 to 4 carbon atoms, an alkylthio group having 1 to 4 carbon atoms, or an alkoxycarbonyl group having 1 to 5 carbon atoms. In addition, $R^5$ represents any of hydrogen, an alkyl group having 1 to 4 carbon atoms, an alkoxy group having 1 to 4 carbon atoms, a halogen group, a haloalkyl group having 1 to 4 carbon atoms, or an aryl group having 6 to 12 carbon atoms. M is a central metal and represents either a Group 9 element or a Group 10 element. Moreover, n is 2 when M is a Group 9 element or n is 1 when M is a Group 10 element.

In the organometallic complex having the structure represented by any of General Formulas (G1) to (G3) above (i.e., including the organometallic complexes represented by General Formulas (G4) to (G9)), α-naphthylpyrazine represented by General Formula (G0) is ortho-metalated with a metal ion. Such a coordinate structure greatly contributes to deep red phosphorescence. Thus, another embodiment of the present invention is a light-emitting material containing the organometallic complex described above.

Further, the organometallic complex of the present invention is very effective for the following reason: the organometallic complex can emit deep red phosphorescence, that is, it can convert triplet excitation energy into emission and can exhibit deep red emission, and therefore higher efficiency is possible when the organometallic complex is applied to a light-emitting element. Thus, the present invention also includes, in its scope, a light-emitting element in which the organometallic complex of the present invention is used.

At this time, the organometallic complex of the present invention is effective in use for a light-emitting substance in terms of emission efficiency. Thus, a light-emitting element in which the organometallic complex of the present invention is used for a light-emitting substance is also a feature of the present invention.

Further, the present invention includes, in its category, not only a light-emitting device having a light-emitting element but also an electronic device having the light-emitting device. The light-emitting device in this specification refers to an image display device, a light-emitting device, and a light source (e.g., a lighting device). In addition, the light-emitting device includes, in its category, all of a module in which a light-emitting device is connected to a connector such as a flexible printed circuit (FPC), a tape automated bonding (TAB) tape or a tape carrier package (TCP), a module in which a printed wiring board is provided on the tip of a TAB tape or a TCP, and a module in which an integrated circuit (IC) is directly mounted on a light-emitting element by a chip on glass (COG) method.

According to one embodiment of the present invention, a novel organometallic complex which can emit phosphorescence can be provided by using an organic compound with which a variety of derivatives can be easily synthesized as a ligand. In addition, according to one embodiment of the present invention, an organometallic complex which exhibits deep red emission can be provided. Moreover, according to one embodiment of the present invention, a light-emitting element, a light-emitting device, and an electronic device in each of which an organometallic complex which exhibits deep red emission is included can be provided.

DETAILED DESCRIPTION OF THE INVENTION

Figure 1:
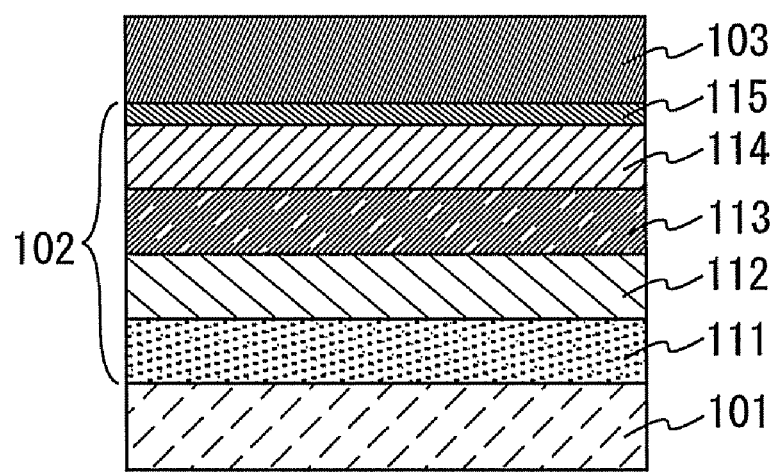
FIG. 1 illustrates a light-emitting element which is one embodiment of the present invention.

Hereinafter, embodiments and examples of the present invention will be described in detail with reference to the accompanying drawings. Note that the present invention is not limited to the description below, and modes and details thereof can be modified in various ways without departing from the spirit and the scope of the present invention. Therefore, the present invention should not be construed as being limited to the description of the following embodiments and examples.

(Embodiment 1)

In Embodiment 1, an organometallic complex which is one embodiment of the present invention will be described.

<<<Synthesis Method of α-Naphthylpyrazine Derivative Represented by General Formula (G0)>>>

The α-naphthylpyrazine derivative represented by General Formula (G0) below can be synthesized by a simple synthesis scheme as described below. The α-naphthylpyrazine derivative can be obtained, for example, by a reaction between a lithium compound of α-naphthyl or a Grignard reagent of α-naphthyl (A1) and a pyrazine compound (A2) as shown in Scheme (a) below. Alternatively, the α-naphthylpyrazine derivative can be obtained by coupling of boronic acid of α-naphthyl compound (A1') and a halogenated pyrazine compound (A2') as shown in Scheme (a') below. Further alternatively, the α-naphthylpyrazine derivative can be obtained by a reaction between diketone of α-naphthyl compound (A1") and diamine (A2") as shown in Scheme (a") below. Note that in the formula, X represents a halogen element.

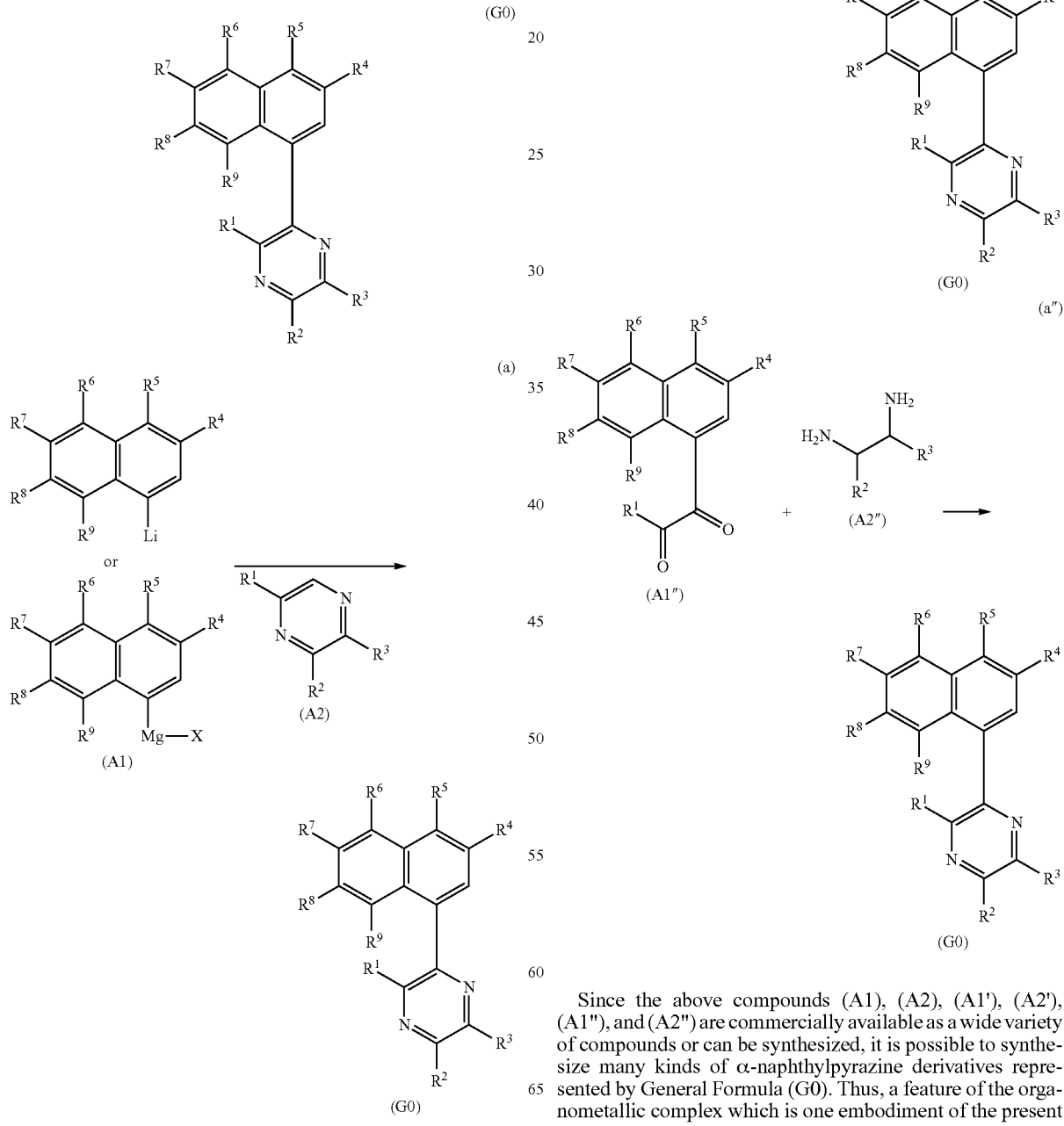

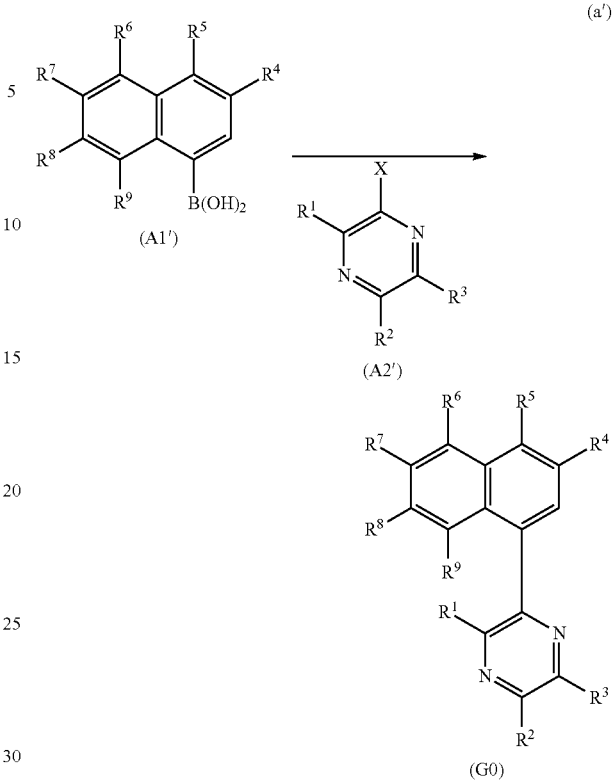

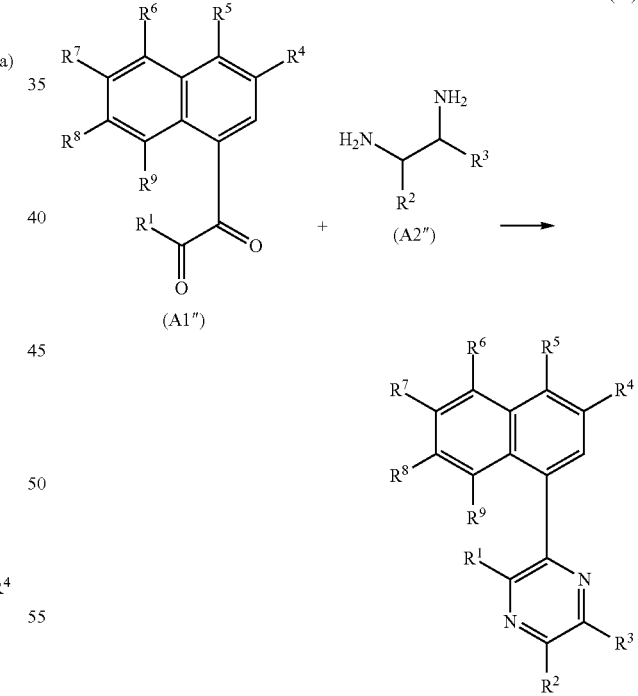

Since the above compounds (A1), (A2), (A1'), (A2'), (A1"), and (A2") are commercially available as a wide variety of compounds or can be synthesized, it is possible to synthesize many kinds of α-naphthylpyrazine derivatives represented by General Formula (G0). Thus, a feature of the organometallic complex which is one embodiment of the present invention is the abundance of ligand variations.

<<Synthesis Method of Organometallic Complex Represented by General Formula (G4)>>

Next described are an organometallic complex represented by General Formula (G4) below and an organometallic complex represented by General Formula (G7), which are specific preferable examples of an organometallic complex of one embodiment of the present invention formed by ortho-metallation of the α-naphthylpyrazine derivative represented by General Formula (G0), i.e., organometallic complex having a structure represented by General Formula (G1) below.

First, as shown in Synthesis Scheme (b) below, the α-naphthylpyrazine derivative represented by General Formula (G0) and a compound of a metal belonging to Group 9 or Group 10 which contains halogen (a metal halide or a metal complex) are heated with an alcohol solvent (e.g., glycerol, ethyleneglycol, 2-methoxyethanol, or 2-ethoxyethanol) alone or a mixed solvent of water and one or more kinds of alcohol solvents, whereby a binuclear complex (B), which is a kind of organometallic complexes having the structure represented by General Formula (G1), can be obtained.

As the compound of a metal belonging to Group 9 or Group 10, which contains halogen, rhodium chloride hydrate, palladium chloride, iridium chloride hydrate, iridium chloride hydrochloride hydrate, potassium tetrachloroplatinate(II), and the like are given; however, the present invention is not limited to these examples. Note that in Synthesis Scheme (b) below, M represents a Group 9 element or Group 10, and X represents a halogen element. In addition, n is 2 when M is a Group 9 element or n is 1 when M is a Group 10 element.

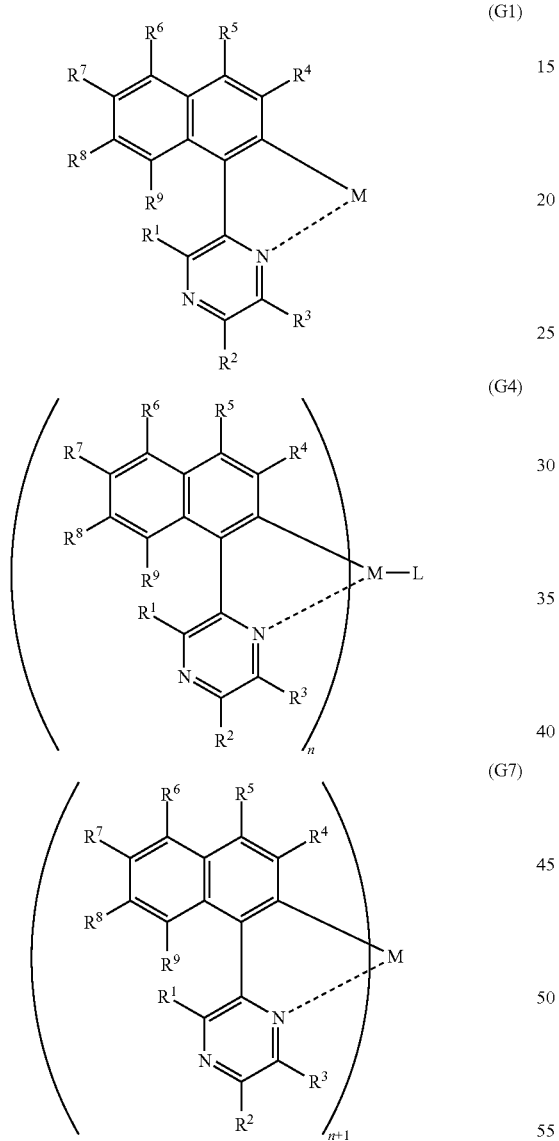

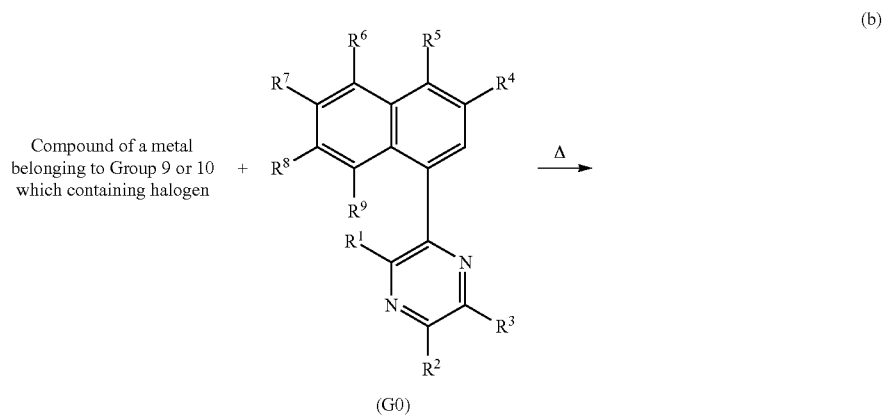

(b)

(G0)

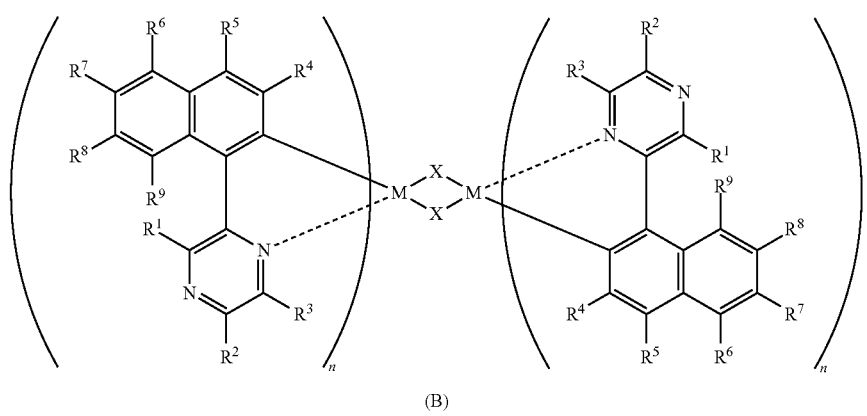

(B)

Furthermore, as shown in Synthesis Scheme (c) below, the dinuclear complex (B) obtained by the above Synthesis Scheme (b) is reacted with HL that is a material of a monoanionic ligand, whereby a proton of HL is eliminated to be coordinated to the central metal M, giving the organometallic complex which is one embodiment of the present invention represented by General Formula (G4). Note that, in Synthesis Scheme (c), M represents a Group 9 element or Group 10, and X represents a halogen element. In addition, n is 2 when M is a Group 9 element or n is 1 when M is a Group 10 element.

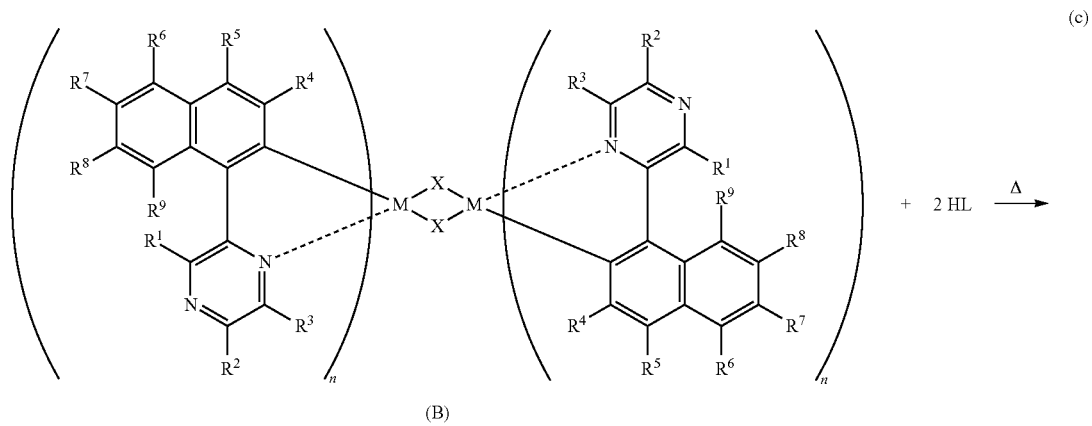

(B)

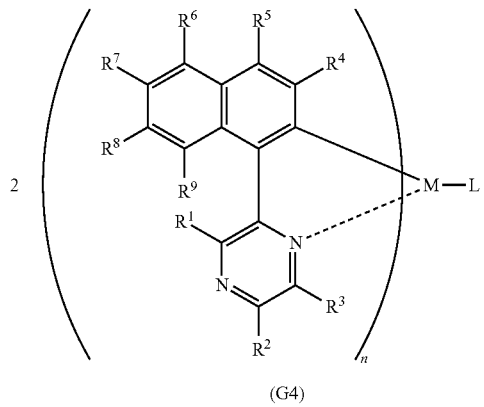

(G4)

In General Formula (G4), $R^1$ and $R^2$ individually represent any of an alkyl group having 1 to 4 carbon atoms, an alkoxy group having 1 to 4 carbon atoms, an allylthio group having 1 to 4 carbon atoms, or an alkoxycarbonyl group having 1 to 5 carbon atoms. $R^3$ represents hydrogen or an alkyl group having 1 to 4 carbon atoms. In addition, $R^4$, $R^5$, $R^6$, $R^7$, $R^8$, and $R^9$ individually represent any of hydrogen, an alkyl group having 1 to 4 carbon atoms, an alkoxy group having 1 to 4 carbon atoms, a halogen group, a haloalkyl group, or an aryl group having 6 to 12 carbon atoms. A pair of adjacent substituents selected from the substituents $R^4$, $R^5$, $R^6$, $R^7$, $R^8$, and $R^9$ may be bonded to each other to form an unsaturated ring structure. M is a central metal and represents either a Group 9 element or a Group 10 element. L represents a monoanionic ligand. Moreover, n is 2 when M is a Group 9 element or n is 1 when M is a Group 10 element. When $R^1$ and $R^2$ is not hydrogen but any substituent such as an alkyl group having 1 to 4 carbon atoms, an alkoxy group having 1 to 4 carbon atoms, an allylthio group having 1 to 4 carbon atoms, or an alkoxycarbonyl group having 1 to 5 carbon atom, decomposition reaction in Scheme (c) can be suppressed, whereby the yield is improved.

The monoanionic ligand (L) in General Formula (G4) is any of a monoanionic bidentate chelate ligand having a β-diketone structure, a monoanionic bidentate chelate ligand having a carboxyl group, a monoanionic bidentate chelate ligand having a phenolic hydroxyl group, or a monoanionic bidentate chelate ligand in which two ligand elements are both nitrogen.

Further, the monoanionic ligand (L) in General Formula (G4) is represented by any of Structural Formulas (L1) to (L6) below.

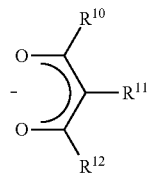

(L1)

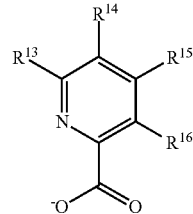

(L2)

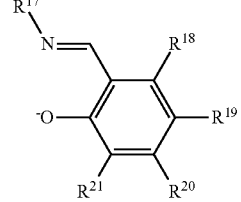

(L3)

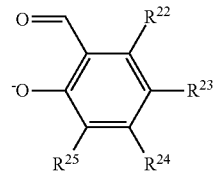

(L4)

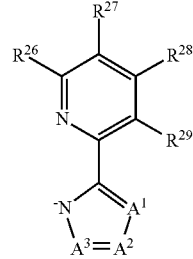

(L5)

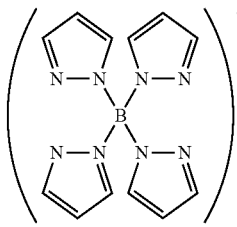

(L6)

In the formula, $R^{10}$ to $R^{29}$ individually represent any of hydrogen, an alkyl group having 1 to 4 carbon atoms, a halogen group, a haloallyl group, an alkoxy group having 1 to 4 carbon atoms, or an alkylthio group having 1 to 4 carbon atoms. In addition, $A^1$, $A^2$, and $A^3$ individually represent nitrogen N or carbon C—R, and R represents hydrogen, an allyl group having 1 to 4 carbon atoms, a halogen group, or a haloalkyl group having 1 to 4 carbon atoms.

The organometallic complex of one embodiment of the present invention, which is represented by the above General Formula (G7), can be synthesized according to Synthesis Scheme (d) below. In other words, the organometallic complex can be obtained by heating the organometallic complex represented by General Formula (G4) which is obtained by the above Synthesis Scheme (c) and the α-naphthylpyrazine derivative represented by General Formula (G0) in a high boiling solvent such as glycerin at a high temperature of about 200° C. Note that, in Synthesis Scheme (d), M represents a Group 9 element or Group 10, and X represents a halogen element. In addition, n is 2 when M is a Group 9 element or n is 1 when M is a Group 10 element.

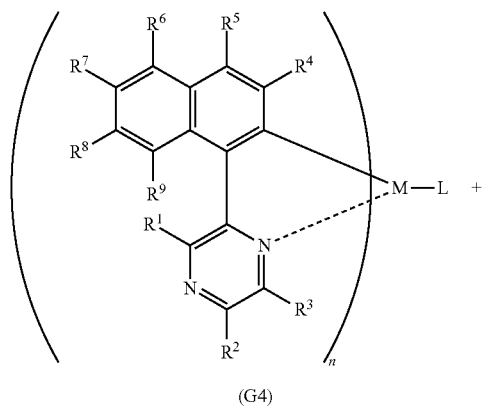

(d)

(G4)

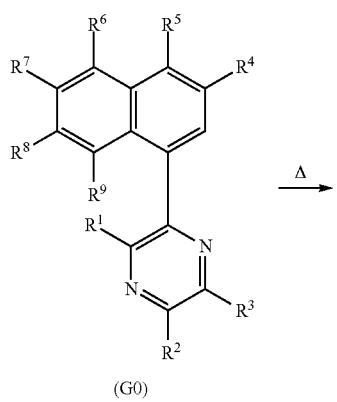

(G0)

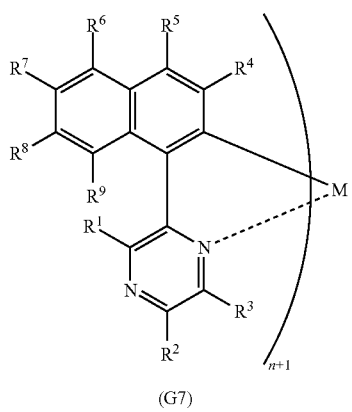

(G7)

In the above General Formula (G7), $R^1$ and $R^2$ individually represent any of an alkyl group having 1 to 4 carbon atoms, an alkoxy group having 1 to 4 carbon atoms, an allylthio group having 1 to 4 carbon atoms, or an alkoxycarbonyl group having 1 to 5 carbon atoms. $R^3$ represents hydrogen or an alkyl group having 1 to 4 carbon atoms. In addition, $R^4$, $R^5$, $R^6$, $R^7$, $R^8$, and $R^9$ individually represent any of hydrogen, an alkyl group having 1 to 4 carbon atoms, an alkoxy group having 1 to 4 carbon atoms, a halogen group, a haloallyl group, or an aryl group having 6 to 12 carbon atoms. A pair of adjacent substituents selected from the substituents $R^4$, $R^5$, $R^6$, $R^7$, $R^8$, and $R^9$ may be bonded to each other to form a saturated ring structure. M is a central metal and represents either a Group 9 element or a Group 10 element. Moreover, n is 2 when M is a Group 9 element or n is 1 when M is a Group 10 element.

The organometallic complex which is one embodiment of the present invention is formed by combining the central metal M and the monoanionic ligand L described above as appropriate. Hereinafter, specific structural formulas of organometallic complexes each of which is one embodiment of the present invention are given (Structural Formulas (100) to (140) below). However, the present invention is not limited thereto.

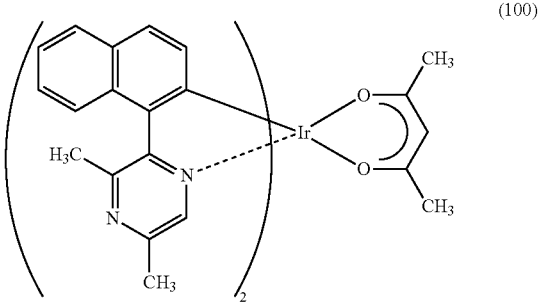

(100)

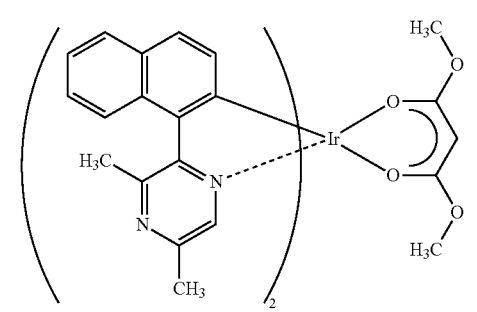
(101)
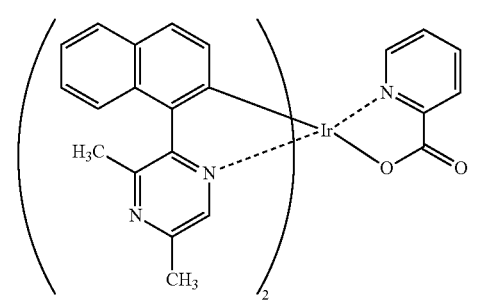
(102)
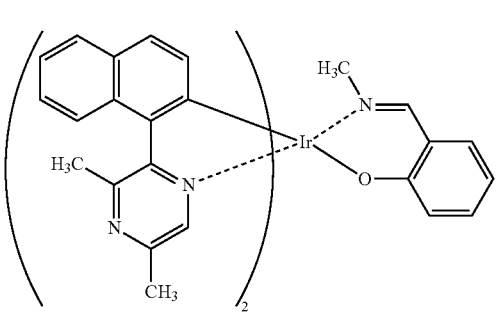
(103)
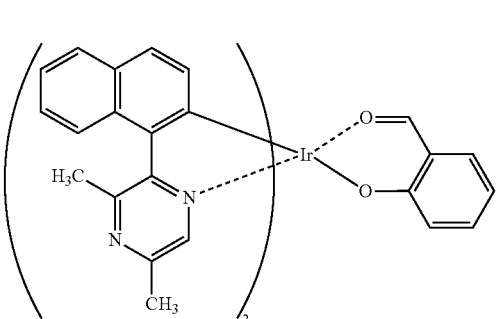
(104)
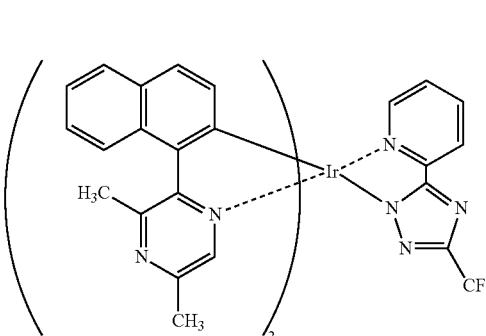
(105)
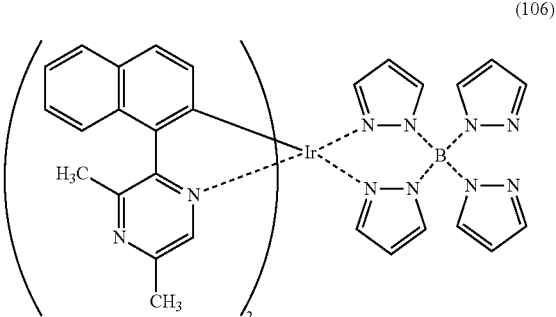
(106)
(107)
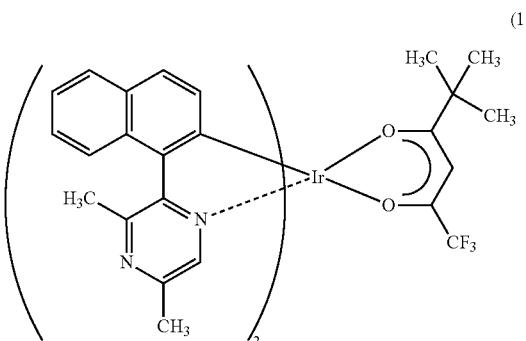
(108)
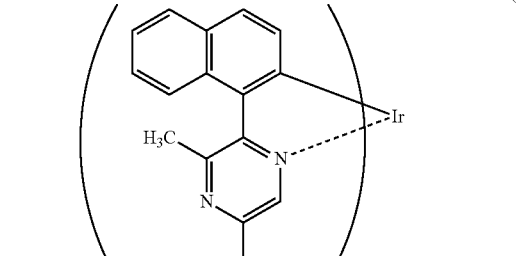
(109)
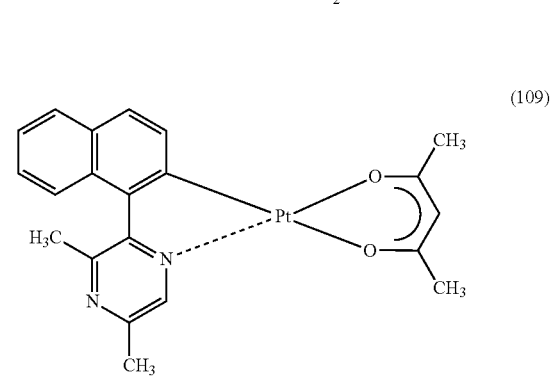
(110)

(111) 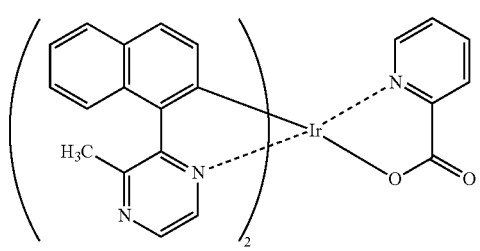
(112) 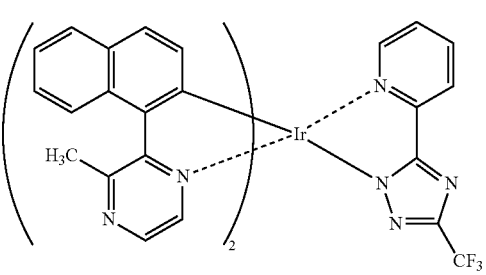
(113) 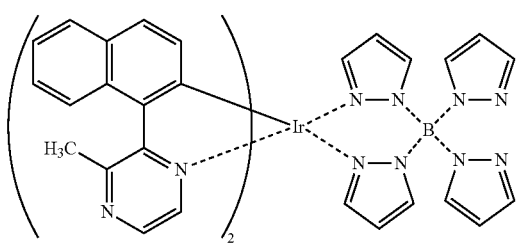
(114) 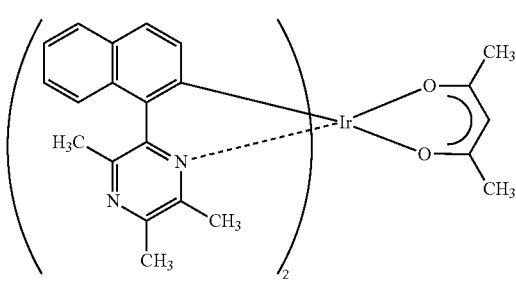
(115) 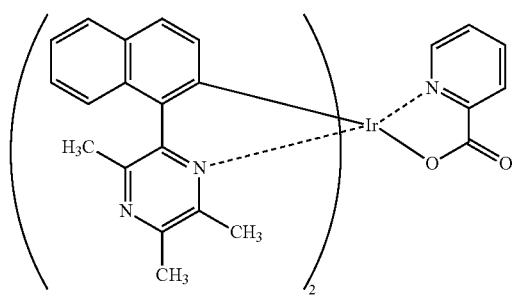
(116) 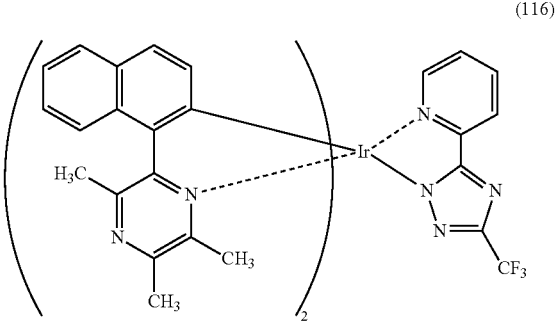
(117) 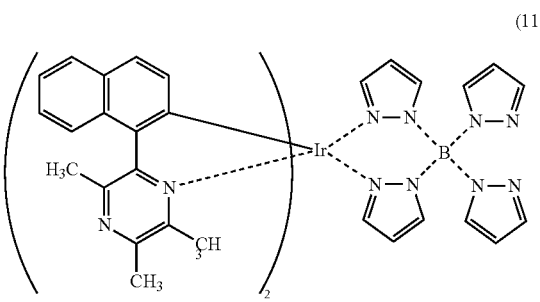
(118) 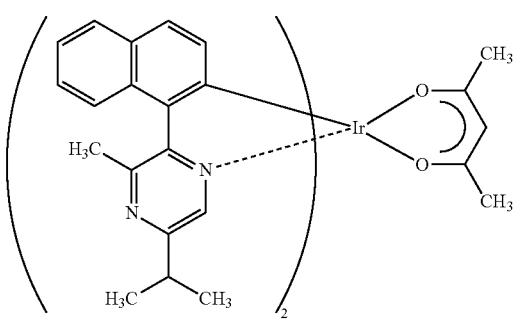
(119) 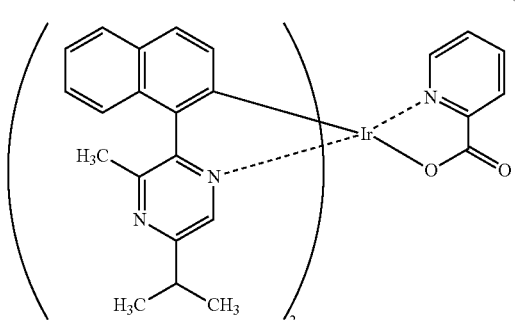
(120) 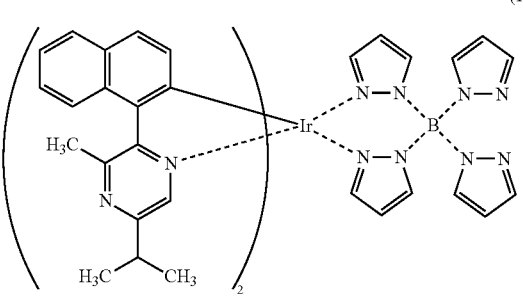

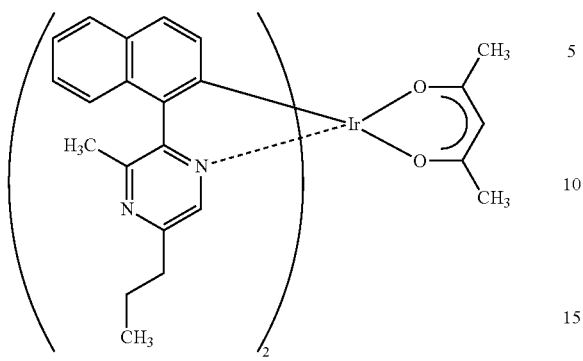
(121)
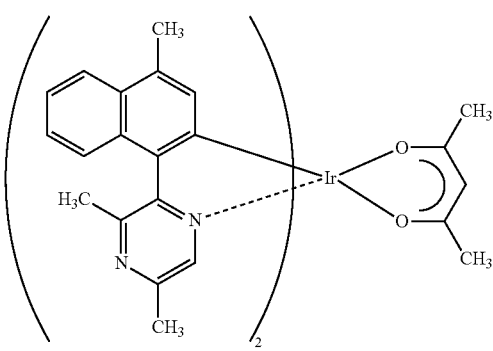
(125)
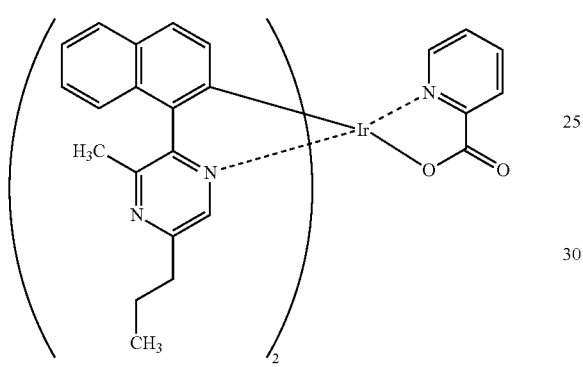
(122)
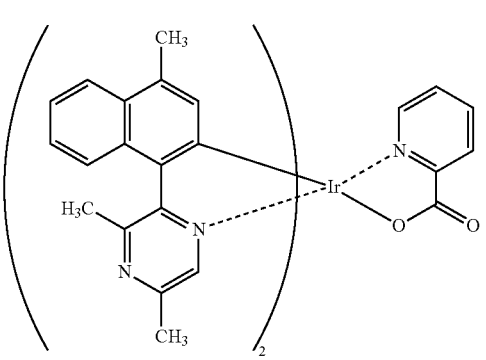
(126)
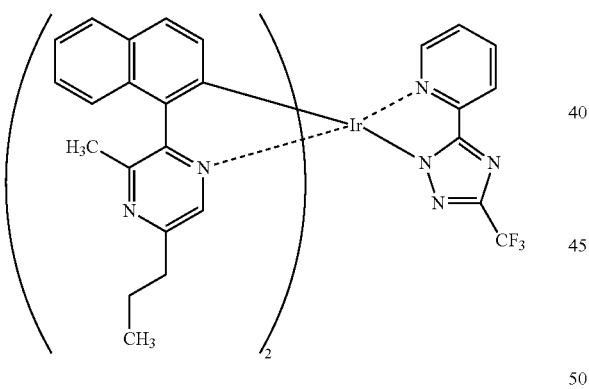
(123)
(127)
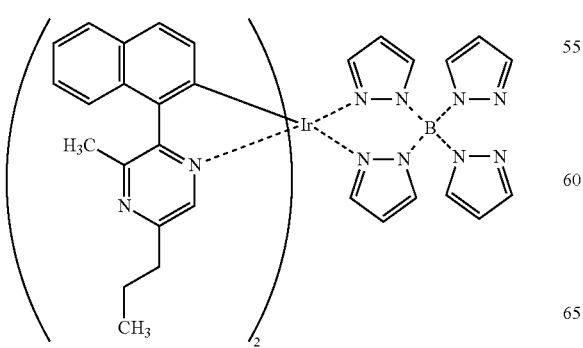
(124)
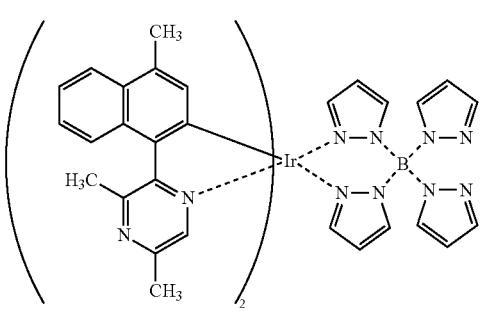
(128)

(129)
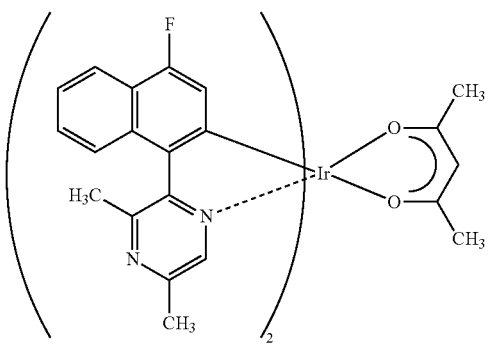
(133)
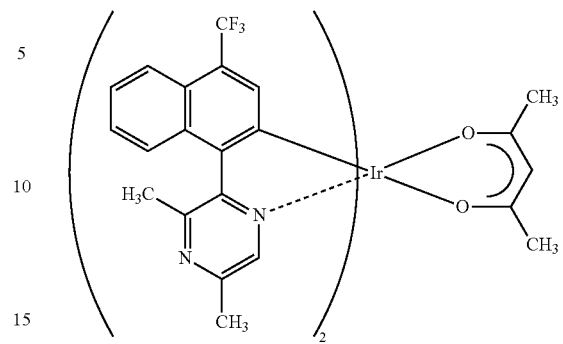
(130)
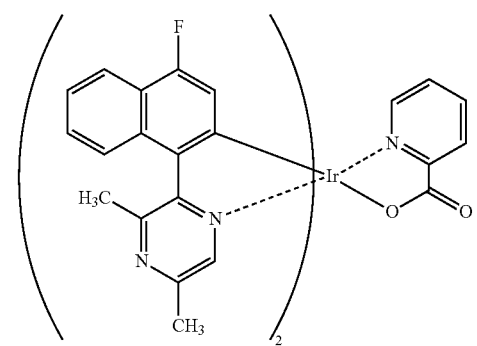
(134)
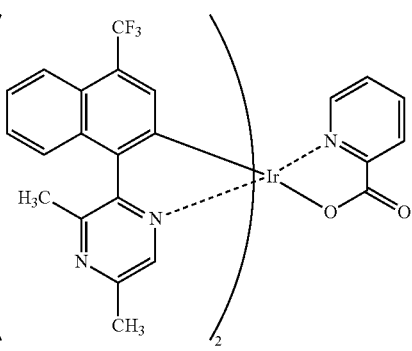
(131)
(135)
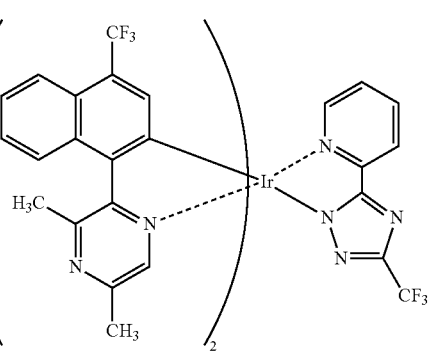
(132)
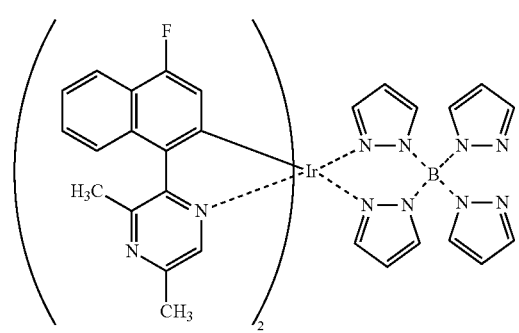
(136)
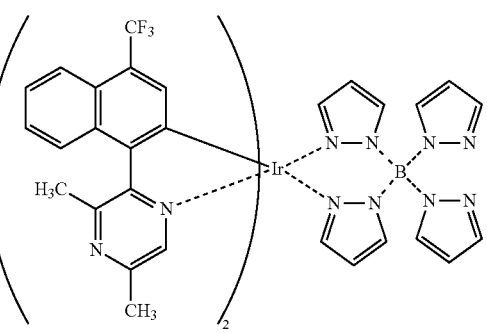

(137)

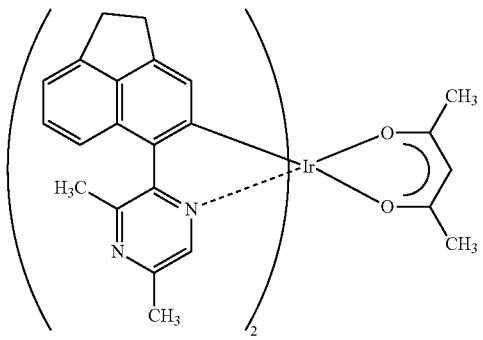

(138)

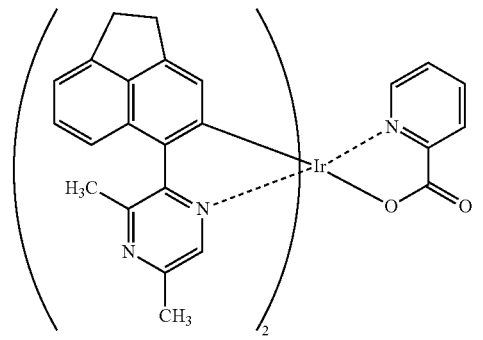

(139)

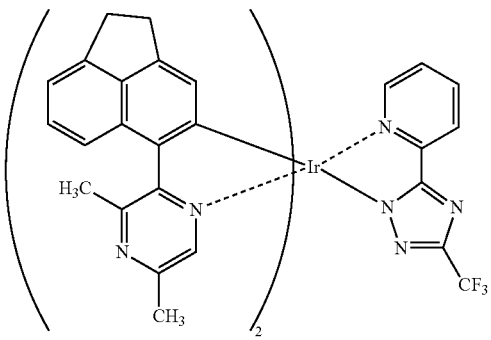

(140)

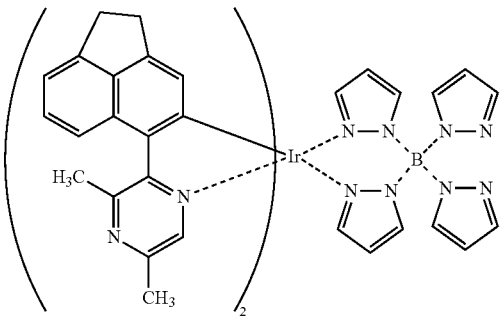

Note that geometrical isomers and stereoisomers which can exist in each of the organometallic complexes represented by the above Structural Formulas (100) to (140) depend on the type of ligand. The organometallic complex of the present invention includes all of these isomers.

Further, the above-described organometallic complexes each of which is one embodiment of the present invention can be used as a photosensitizer owing to its capability of inter- system crossing. In addition, the organometallic complexes are capable of emitting phosphorescence, and therefore can be used as a light-emitting material or a light-emitting substance for a light-emitting element.

(Embodiment 2)

In this embodiment, as one embodiment of the present invention, a light-emitting element in which an organometallic complex is used for a light-emitting layer will be described with reference to FIG. 1.

FIG. 1 illustrates a light-emitting element in which an EL layer 102 including a light-emitting layer 113 is interposed between a first electrode 101 and a second electrode 103. The light-emitting layer 113 contains the organometallic complex which is one embodiment of the present invention, which has been described in Embodiment 1.

By application of a voltage to such a light-emitting element, holes injected from the first electrode 101 side and electrons injected from the second electrode 103 side recombine in the light-emitting layer 113 to bring the organometallic complex into an excited state. Light is emitted when the organometallic complex in the excited state returns to the ground state. Thus, the organometallic complex which is one embodiment of the present invention functions as a light-emitting substance in the light-emitting element. Note that, in the light-emitting element described in this embodiment, the first electrode 101 functions as an anode and the second electrode 103 functions as a cathode.

When the first electrode 101 functions as an anode, it is preferably formed using a metal, an alloy, an electrically-conductive compound, a mixture thereof, or the like each having a high work function (specifically, a work function of 4.0 eV or more). Specifically, for example, indium tin oxide (ITO), indium tin oxide containing silicon or silicon oxide, indium zinc oxide (IZO), indium oxide containing tungsten oxide and zinc oxide, and the like can be given. Other than the above, gold (Au), platinum (Pt), nickel (Ni), tungsten (W), chromium (Cr), molybdenum (Mo), iron (Fe), cobalt (Co), copper (Cu), palladium (Pd), titanium (Ti), or the like can be used.

Note that, in the case where in the EL layer 102, a layer formed in contact with the first electrode 101 is formed using a composite material in which an organic compound and an electron acceptor (acceptor) which are described later are mixed, the first electrode 101 can be formed using any of various types of metals, alloys, and electrically-conductive compounds, a mixture thereof, and the like regardless of the work function. For example, aluminum (Al), silver (Ag), an alloy containing aluminum (e.g., AlSi), or the like can be used.

The first electrode 101 can be formed by, for example, a sputtering method, an evaporation method (e.g., a vacuum evaporation method), or the like.

The EL layer 102 formed over the first electrode 101 includes at least the light-emitting layer 113 and contains an organometallic complex which is one embodiment of the present invention. For part of the EL layer 102, a known substance can be used, and either a low molecular compound or a high molecular compound can be used. Note that the substance used for forming the EL layer 102 may have not only a structure formed of only an organic compound but also a structure in which an inorganic compound is partially contained.

Further, as illustrated in FIG. 1, the EL layer 102 is formed by stacking as appropriate a hole-injection layer 111 containing a substance having a high hole-transport property, a hole-transport layer 112 containing a substance having a high hole-transport property, an electron-transport layer 114 containing a substance having a high electron-transport property, an electron-injection layer 115 containing a substance having a high electron-injection property, and the like in addition to the light-emitting layer 113.

The hole-injection layer 111 is a layer containing a substance having a high hole-injection property. As the substance having a high hole-injection property, metal oxide such as molybdenum oxide, titanium oxide, vanadium oxide, rhenium oxide, ruthenium oxide, chromium oxide, zirconium oxide, hafnium oxide, tantalum oxide, silver oxide, tungsten oxide, or manganese oxide can be used. Alternatively, a phthalocyanine compound such as phthalocyanine (abbreviation: $H_2Pc$), copper(II) phthalocyanine (abbreviation: CuPc), or vanadyl phthalocyanine (abbreviation: VOPc) can be used.

Alternatively, the following aromatic amine compounds which are low molecular organic compounds can be used: 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphtyl)-N-(9-phenylcarbazol-3-yl)amino]-9-phenylcarbazole (abbreviation: PCzPCN1), or the like.

Further alternatively, a high molecular compound (e.g., an oligomer, a dendrimer, or a polymer) can be used. For example, a high molecular compound such as poly(N-vinylcarbazole) (abbreviation: PVK), poly(4-vinyltriphenylamine) (abbreviation: PVTPA), poly[N-(4-{N'-[4-(4-diphenylamino}phenyl]phenyl-N'-phenylamino]phenyl) methacrylamide] (abbreviation: PTPDMA), or poly[N,N'-bis(4-butylphenyl)-N,N'-bis(phenyl)benzidine (abbreviation: poly-TPD) can be given. Further alternatively, a high molecular compound doped with acid, such as poly(3,4-ethylenedioxythiophene)/poly(styrenesulfonic acid) (PEDOT/PSS) or polyanline/poly(styrenesulfonic acid) (PAni/PSS) can be used.

A composite material in which an organic compound and an electron acceptor (acceptor) are mixed may be used for the hole-injection layer 111. Such a composite material is excellent in a hole-injection property and a hole-transport property because holes are generated in the organic compound by the electron acceptor. In this case, the organic compound is preferably a material excellent in transporting the generated holes (a substance having a high hole-transport property).

As the organic compound used for the composite material, a variety of compounds such as an aromatic amine compound, a carbazole derivative, an aromatic hydrocarbon, and a high molecular compound (e.g., an oligomer, a dendrimer, or a polymer) can be used. Note that the organic compound used for the composite material preferably has a high hole-transport property. Specifically, a substance having a hole mobility of $10^{-6}$ cm$^2$/Vs or more is preferable. However, materials other than these may alternatively be used as long as they have a hole-transport property higher than an electron-transport property. Specific examples of the organic compound that can be used for the composite material will be given below.

As the organic compound that can be used for the composite material, for example, an aromatic amine compound such as TDATA, MIDATA, DPAB, DNTPD, DPA3B, PCzPCA1, PCzPCA2, PCzPCN1, 4,4'-bis[N-(1-naphtyl)-N-phenylamino]biphenyl (abbreviation: NPB or α-NPD), or N,N'-bis(3-methylphenyl)-N,N'-diphenyl-[1,1'-biphenyl]-4,4'-diamine (abbreviation: TPD); and a carbazole derivative such as 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)]phenyl-10-phenylanthracene (abbreviation: CzPA), or 1,4-bis[4-(N-carbazolyl)phenyl]-2,3,5,6-tetraphenylbenzene can be used.

Alternatively, an aromatic hydrocarbon compound such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, or 2,3,6,7-tetramethyl-9,10-di(1-naphthyl)anthracene can be used.

Further alternatively, an aromatic hydrocarbon compound such as 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), or 9,10-bis[4-(2,2-diphenylvinyl)phenyl]anthracene (abbreviation: DPVPA) can be used.

Further, as the electron acceptor, organic compounds such as 7,7,8,8-tetracyano-2,3,5,6-tetrafluoroquinodimethane (abbreviation: $F_4$-TCNQ) and chloranil; and transition metal oxides can be given. In addition, oxides of metals belonging to Group 4 to Group 8 of the periodic table can also be given. Specifically, vanadium oxide, niobium oxide, tantalum oxide, chromium oxide, molybdenum oxide, tungsten oxide, manganese oxide, and rhenium oxide are preferable because they have a high electron-accepting property. Among the above, molybdenum oxide is especially preferable because it is stable in the air, has low hygroscopic property, and is easy to handle.

Note that the hole-injection layer 111 may be formed using a composite material of the above-described high molecular compound, such as PVK, PVTPA, PTPDMA, or Poly-TPD, and the above-described electron acceptor.

The hole-transport layer 112 is a layer containing a substance having a high hole-transport property. As the substance having a high hole-transport property, an aromatic amine compound such as NPB, TPD, 4,4'-bis[N-(9,9-dimethylfluoren-2-yl)-N-phenylamino]biphenyl (abbreviation: DFLDPBi), or 4,4'-bis[N-(spiro-9,9'-bifluoren-2-yl)-N-phenylamino]biphenyl (abbreviation: BSPB) can be used. The materials described here are mainly materials having a hole mobility of $10^{-6}$ cm$^2$/Vs or higher. However, substances other than these can also be used as long as they have a hole-transport property higher than an electron-transport property. Note that the layer containing a substance having a high hole-transport property is not limited to a single layer, and a stacked layer in which two or more layers containing the above-described substance are stacked may be used.

Alternatively, for the hole-transport layer 112, a high molecular compound such as PVK, PVTPA, PTPDMA, or Poly-TPD can be used.

The light-emitting layer 113 is preferably a layer containing the organometallic complex which is one embodiment of the present invention, specifically, a layer containing, as a host, a substance which has a higher triplet excitation energy than the organometallic complex which is one embodiment of the present invention and the organometallic complex which is one embodiment of the present invention dispersed as a guest. Thus, quenching of light emission from the organometallic complex caused due to the concentration can be prevented. Note that the triplet excitation energy indicates an energy gap between a ground state and a triplet excited state.

Although there is no particular limitation on the substance used for dispersing any of the above-described organometallic complexes (i.e., a host), a carbazole derivative such as CBP or 4,4',4''-tris(N-carbazolyl)triphenylamine (abbreviation: TCTA); and a metal complex such as bis[2-(2-hydroxyphenyl)pyridinato]zinc (abbreviation: $Znpp_2$), bis[2-(2-hydroxyphenyl)benzoxazolato]zinc (abbreviation: ZnBOX), bis(2-methyl-8-quinolinolato)(4-phenylphenolato)aluminum (abbreviation: BAlq), or tris(8-quinolinolato)aluminum (abbreviation: $Alq_3$) are preferable in addition to a compound having an arylamine skeleton, such as 2,3-bis(4-diphenylaminophenyl)quinoxaline (abbreviation: TPAQn) or NPB. Alternatively, a high molecular compound such as PVK can be used.

The electron-transport layer 114 is a layer containing a substance having a high electron-transport property. For the electron-transport layer 114, metal complexes such as $Alq_3$, tris(4-methyl-8-quinolinolato)aluminum (abbreviation: $Almq_3$), bis(10-hydroxybenzo[h]quinolinato)beryllium (abbreviation: $BeBq_2$), BAlq, $Zn(BOX)_2$, or bis[2-(2'-hydroxyphenyl)pyridinato]zinc (abbreviation: $Zn(BTZ)_2$) can be given. Alternatively, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yp-stilbene (abbreviation: BzOs) can be used. Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy) can be used. The substances described here are mainly materials having an electron mobility of $10^{-6}$ $cm^2/Vs$ or more. Note that materials other than these may alternatively be used as long as they have an electron-transport property higher than a hole-transport property.

Further, the electron-transport layer is not limited to a single layer, and a stacked layer in which two or more layers containing any of the above-described substances are stacked may be used.

The electron-injection layer 115 is a layer containing a substance having a high electron-injection property. For the electron-injection layer 115, an alkali metal, an alkaline earth metal, or a compound thereof, such as lithium fluoride (LiF), cesium fluoride (CsF), calcium fluoride ($CaF_2$), or lithium oxide (LiOx), can be used. Alternatively, a rare earth metal compound such as erbium fluoride ($ErF_3$) can be used. Further alternatively, the substances for forming the electron-transport layer 114, which are described above, can be used.

Alternatively, a composite material in which an organic compound and an electron donor (donor) are mixed may be used for the electron-injection layer 115. Such a composite material is excellent in an electron-injection property and an electron-transport property because electrons are generated in the organic compound by the electron donor. In this case, the organic compound is preferably a material excellent in transporting the generated electrons. Specifically, for example, the substances for forming the electron-transport layer 114 (e.g., a metal complex and a heteroaromatic compound), which are described above, can be used. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, ytterbium, and the like are given. In addition, alkali metal oxide or alkaline earth metal oxide such as lithium oxide, calcium oxide, barium oxide, and the like can be given. Lewis base such as magnesium oxide can alternatively be used. An organic compound such as tetrathiafulvalene (abbreviation: TTF) can alternatively be used.

Note that each of the above-described hole-injection layer 111, hole-transport layer 112, light-emitting layer 113, electron-transport layer 114, and electron-injection layer 115 can be formed by a method such as an evaporation method (e.g., a vacuum evaporation method), an ink-jet method, or a coating method.

When the second electrode 103 functions as a cathode, it can be formed using a metal, an alloy, an electrically-conductive compound, a mixture thereof, or the like having a low work function (preferably, a work function of 3.8 eV or less). Specifically, Al, silver, or the like can be used besides an element belonging to Group 1 or Group 2 of the periodic table, that is, an alkali metal such lithium (Li) or cesium (Cs) and an alkaline earth metal such as magnesium (Mg), calcium (Ca), or strontium (Sr); an alloy of the above metals (e.g., MgAg and AlLi); a rare earth metal such as europium (Eu) or ytterbium (Yb); an alloy of the above metals, or the like.

Note that, in the case where in the EL layer 102, a layer formed in contact with the second electrode 103 is formed using a composite material in which the organic compound and the electron donor (donor), which are described above, are mixed, a variety of conductive materials such as Al, Ag, ITO, and indium tin oxide containing silicon or silicon oxide can be used regardless of the work function.

Note that the second electrode 103 can be formed by a vacuum evaporation method or a sputtering method. Alternatively, in the case of using a silver paste or the like, a coating method, an ink-jet method, or the like can be used.

In the above-described light-emitting element, current flows due to a potential difference generated between the first electrode 101 and the second electrode 103 and holes and electrons recombine in the EL layer 102, whereby light is emitted. Then, the emitted light is extracted outside through one or both of the first electrode 101 and the second electrode 103. Therefore, one or both of the first electrode 101 and the second electrode 103 are electrodes having a light-transmitting property.

Note that by use of the light-emitting element described in this embodiment, a passive matrix light-emitting device or an active matrix light-emitting device in which the driving of the light-emitting element is controlled by a thin film transistor (TFT) can be manufactured.

Note that there is no particular limitation on the structure of the TFT in the case of manufacturing the active matrix light-emitting device. For example, a staggered TFT or an inverted staggered TFT can be used as appropriate. Further, a driver circuit formed over a TFT substrate may be formed of both an n-type TFT and a p-type TFT or only either an n-type TFT or a p-type TFT. Furthermore, there is also no particular limitation on crystallinity of a semiconductor film used for the TFT.

For example, an amorphous semiconductor film, a crystalline semiconductor film, an oxide semiconductor film, or the like can be used.

Note that, in this embodiment, the organometallic complex of one embodiment of the present invention, which is used for the light-emitting layer 113, exhibits deep red emission with excellent color purity. Thus, a light-emitting element which exhibits deep red emission with excellent color purity can be obtained.

The structure described in Embodiment 2 can be combined with the structure described in Embodiment 1 as appropriate.

(Embodiment 3)

The light-emitting element which is one embodiment of the present invention may include a plurality of light-emitting layers. A plurality of light-emitting layers are provided and light is emitted from each of the light-emitting layers, whereby emission in which plural types of light are mixed can be obtained. Thus, white light can be obtained, for example. In this embodiment, an embodiment of a light-emitting element including a plurality of light-emitting layers will be described with reference to FIG. 2.

Figure 2:
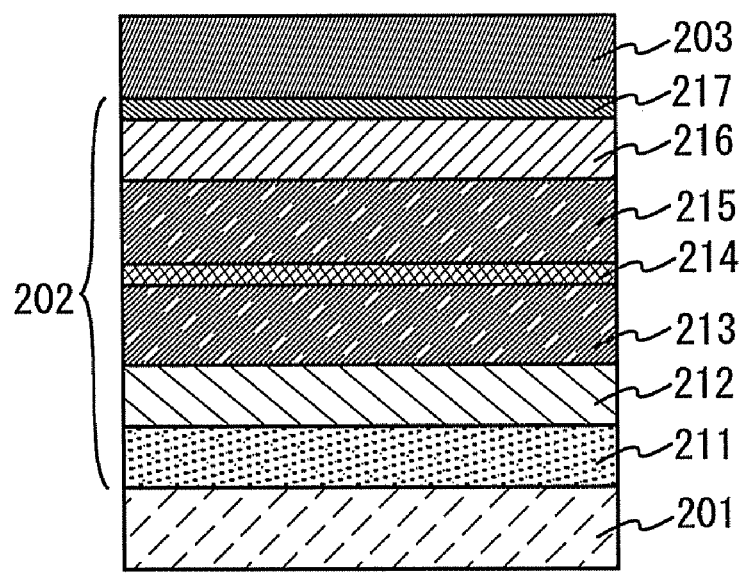
FIG. 2 illustrates a light-emitting element which is one embodiment of the present invention.

In FIG. 2, an EL layer 202 including a first light-emitting layer 213 and a second light-emitting layer 215 is provided between a first electrode 201 and a second electrode 203. Emission in which light emitted from the first light-emitting layer 213 and light emitted from the second light-emitting layer 215 are mixed can be obtained. A separation layer 214 is preferably provided between the first light-emitting layer 213 and the second light-emitting layer 215.

When a voltage is applied so that the potential of the first electrode 201 is higher than the potential of the second electrode 203, current flows between the first electrode 201 and the second electrode 203, and holes and electrons recombine in the first light-emitting layer 213, the second light-emitting layer 215, or in the separation layer 214. Generated excitation energy is distributed to the first light-emitting layer 213 and the second light-emitting layer 215 to bring each of a first light-emitting substance contained in the first light-emitting layer 213 and a second light-emitting substance contained in the second light-emitting layer 215 into an excited state. The excited first and second light-emitting substances emit light when returning to the ground state.

The first light-emitting layer 213 contains the first light-emitting substance typified by a fluorescent compound such as perylene, 2,5,8,11-tetra(tert-butyl)perylene (abbreviation: TBP), DPVBi, 4,4'-bis[2-(N-ethylcarbazol-3-yl)vinyl]biphenyl (abbreviation: BCzVBi), BAlq, or bis(2-methyl-8-quinolinolato)galliumchloride (abbreviation: Gamq$_2$Cl); or a phosphorescent substance such as bis{2-[3,5-bis(trifluoromethyl)phenyl]pyridinato-N,C$^{2'}$}iridium(III)picolinate (abbreviation: Ir(CF$_3$ ppy)$_2$(pic)), bis[2-(4,6-difluorophenyl)pyridinato-N,C$^{2'}$]iridium(III)acetylacetonate (abbreviation: FIr(acac)), bis[2-(4,6-difluorophenyl)pyridinato-N,C$^{2'}$]iridium(III)picolinate (abbreviation: FIrpic), or bis[2-(4,6-difluorophenyl)pyridinato-N,C$^{2'}$]iridium(III)tetra(1-pyrazolyl)borate (abbreviation: FIr6), from which emission having a peak at 450 nm to 510 nm in an emission spectrum (i.e., blue light to blue green light) can be obtained.

Further, in the case where the first light-emitting substance is a fluorescent compound, the first light-emitting layer 213 preferably has a structure in which a substance having a larger singlet excitation energy than the first light-emitting substance is used as a first host and the first light-emitting substance is dispersed as a guest. Further, in the case where the first light-emitting substance is a phosphorescent compound, the first light-emitting layer 213 preferably has a structure in which a substance having a higher triplet excitation energy than the first light-emitting substance is used as a first host and the first light-emitting substance is dispersed as a guest. As the first host, DNA, t-BuDNA, or the like can be used in addition to the above-described NPB, CBP, TCTA, and the like. Note that the singlet excitation energy is an energy difference between a ground state and a singlet excited state. In addition, the triplet excitation energy is an energy difference between a ground state and a triplet excited state.

On the other hand, the second light-emitting layer 215 contains the organometallic complex which is one embodiment of the present invention and can exhibit deep red emission. The second light-emitting layer 215 may have a similar structure to the light-emitting layer 113 described in Embodiment 2.

In addition, specifically, the separation layer 214 can be formed using TPAQn, NPB, CBP, TCTA, Znpp$_2$, ZnBOX, or the like described above. In this way, with provision of the separation layer 214, a defect that emission intensity of one of the first light-emitting layer 213 and the second light-emitting layer 215 is stronger than the other can be prevented. Note that the separation layer 214 is not necessarily provided, and it may be provided as appropriate such that the ratio in emission intensity of the first light-emitting layer 213 to the second light-emitting layer 215 can be adjusted.

Note that, in this embodiment, the organometallic complex which is one embodiment of the present invention is used for the second light-emitting layer 215 and another light-emitting substance is used for the first light-emitting layer 213, whereas the organometallic complex which is one embodiment of the present invention may be used for the first light-emitting layer 213 and another light-emitting substance may be used for the second light-emitting layer 215.

Further, the light-emitting element in which two light-emitting layers are provided as illustrated in FIG. 2 is described in this embodiment; however, the number of the light-emitting layers is not limited to two, and may be, for example, three. Emission from each light-emitting layer may be mixed. As a result, for example, white color emission can be obtained.

Note that the first electrode 201 may have a structure similar to that of the first electrode 101 described in Embodiment 2. In addition, the second electrode 203 may also have a structure similar to that of the second electrode 103 described in Embodiment 2.

Further, in this embodiment, as illustrated in FIG. 2, a hole-injection layer 211, a hole-transport layer 212, an electron-transport layer 216, and an electron-injection layer 217 are provided. As for structures of these layers, the structures of the respective layers described in Embodiment 2 may be applied. However, these layers are not necessarily provided and may be provided according to element characteristics.

Note that the structure described in this embodiment can be combined with the structure described in Embodiment 1 or 2 as appropriate.

(Embodiment 4)

Figure 3:
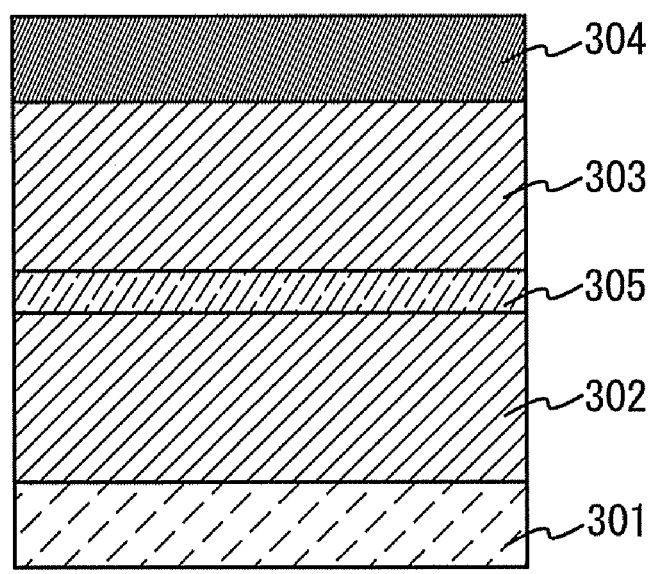
FIG. 3 illustrates a light-emitting element which is one embodiment of the present invention.

In this embodiment, as one embodiment of the present invention, a structure of a light-emitting element in which a plurality of EL layers are included (hereinafter, such a light-emitting element is referred to as a stacked-type element) will be described with reference to FIG. 3. This light-emitting element is a stacked-type light-emitting element including a plurality of EL layers (a first EL layer 302 and a second EL layer 303) between a first electrode 301 and a second electrode 304. Note that, although the structure in which two EL layers are formed is described in this embodiment, a structure in which three or more EL layers are formed may be employed.

In this embodiment, the first electrode 301 functions as an anode, and the second electrode 304 functions as a cathode. Note that for the first electrode 301 and the second electrode 304, structures similar to those described in Embodiment 2 can be employed. In addition, although the plurality of EL layers (the first EL layer 302 and the second EL layer 303) may have structures similar to those described in Embodiment 2, any of the EL layers may have a structure similar to that described in Embodiment 2. In other words, the structures of the first EL layer 302 and the second EL layer 303 may be the same or different from each other and can be similar to those described in Embodiment 2.

Further, a charge generation layer 305 is provided between the plurality of EL layers (the first EL layer 302 and the second EL layer 303). The charge generation layer 305 has a function of injecting electrons into one of the EL layers and injecting holes into the other of the EL layers when a voltage is applied to the first electrode 301 and the second electrode 304. In this embodiment, when a voltage is applied so that the potential of the first electrode 301 is higher than that of the second electrode 304, the charge generation layer 305 injects electrons into the first EL layer 302 and injects holes into the second EL layer 303.

Note that the charge generation layer 305 preferably has a light-transmitting property in terms of light extraction efficiency. Further, the charge generation layer 305 functions even if it has lower conductivity than the first electrode 301 or the second electrode 304.

The charge generation layer 305 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The materials described here are mainly materials having a hole mobility of $10^{-6}$ cm$^2$/Vs or higher. However, substances other than the above substances may be used as long as they are organic compounds having a hole-transport property higher than an electron-transport property.

Further, as the electron acceptor, 7,7,8,8-tetracyano-2,3,5,6-tetrafluoroquinodimethane (abbreviation: F$_4$-TCNQ), chloranil, and the like can be given. In addition, transition metal oxides can be given. Moreover, oxides of metals belonging to Groups 4 to 8 of the periodic table can be used. Specifically, vanadium oxide, niobium oxide, tantalum oxide, chromium oxide, molybdenum oxide, tungsten oxide, manganese oxide, and rhenium oxide are preferable because they have high electron-accepting properties. Among these, molybdenum oxide is especially preferable because it is stable in the air, has low hygroscopic property, and is easy to handle.

On the other hand, in the case of the structure in which an electron donor is added to an organic compound having a high electron-transport property, as the organic compound having a high electron-transport property, for example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$ can be used. Alternatively, in addition to such a metal complex, PBD, OXD-7, TAZ, BPhen, BCP, or the like can be used. The materials described here are mainly materials having an electron mobility of $10^{-6}$ cm$^2$/Vs or higher. Note that substances other than the above substances may be used as long as they are organic compounds having an electron-transport property higher than a hole-transport property.

Further, as the electron donor, an alkali metal, an alkaline earth metal, a rare earth metal, a metal belonging to Group 13 of the periodic table, or an oxide or carbonate thereof can be used. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that by formation of the charge generation layer 305 using any of the above materials, an increase in the drive voltage in the case where the EL layers are stacked can be suppressed.

Although the light-emitting element having two EL layers has been described in this embodiment, the present invention can be similarly applied to a light-emitting element in which three or more EL layers are stacked. A plurality of EL layers are arranged to be separated from each other with a charge generation layer between a pair of electrodes, like the light-emitting element according to this embodiment, whereby an element having a long lifetime and high luminance can be achieved with current density kept low. When the light-emitting element is applied to a lighting device, a drop in voltage due to the resistance of an electrode material can be suppressed, and thus uniform emission in a large area can be achieved. Moreover, a light-emitting device which can be driven at a low voltage and has low power consumption can be achieved.

Further, when the EL layers have different emission colors, a desired emission color can be obtained from the whole light-emitting element. For example, in the light-emitting element having two EL layers, when an emission color of the first EL layer and an emission color of the second EL layer are made to be complementary colors, it is possible to obtain a light-emitting element from which white light is emitted from the whole light-emitting element. Note that "complementary color" refers to a relation between colors which become achromatic color by being mixed. In other words, white emission can be obtained by mixture of light obtained from substances whose emission colors are complementary colors.

Also in a light-emitting element having three EL layers, for example, white light can be similarly obtained from the whole light-emitting element when an emission color of a first EL layer is red, an emission color of a second EL layer is green, and an emission color of a third EL layer is blue.

Note that the structure described in this embodiment can be used in appropriate combination with any structure described in Embodiments 1 and 2.

(Embodiment 5)

In this embodiment, as one embodiment of the present invention, an embodiment of a light-emitting element in which an organometallic complex is used as a sensitizer will be described with reference to FIG. 1.

FIG. 1 illustrates the light-emitting element in which the EL layer 102 including the light-emitting layer 113 is interposed between the first electrode 101 and the second electrode 103. The light-emitting layer 113 contains the organometallic complex which is one embodiment of the present invention and a fluorescent compound which can emit light with a longer wavelength than that of the light emitted from this organometallic complex.

In such a light-emitting element, holes injected from the first electrode 101 and electrons injected from the second electrode 103 side recombine in the light-emitting layer 113 to bring the fluorescent compound into an excited state. Light is emitted when the fluorescent compound in the excited state returns to the ground state. In this case, the organometallic complex which is one embodiment of the present invention acts as a sensitizer for the fluorescent compound to increase the number of molecules of the fluorescent compound in the singlet excited state. As described above, the organometallic complex of the present invention is used as a sensitizer, whereby a light-emitting element with good emission efficiency can be obtained. Note that in the light-emitting element of this embodiment, the first electrode 101 functions as an anode and the second electrode 103 function as a cathode.

The light-emitting layer 113 contains the organometallic complex which is one embodiment of the present invention and the fluorescent compound which can emit light with a longer wavelength than this organometallic complex. The light-emitting layer 113 may have a structure in which a substance having a larger singlet excitation energy than the fluorescent substance as well as a higher triplet excitation energy than the organometallic complex is used as a host, and the organometallic complex and the fluorescent compound are dispersed as a guest.

Note that there is no particular limitation on the substance used for dispersing the organometallic complex and the fluorescent compound (i.e., host), and the substances given as examples of the host in Embodiment 2, or the like can be used.

Further, although there is also no particular limitation on the fluorescent compound, a compound which can exhibit emission of deep red light to deep red infrared light, such as 4-dicyanomethylene-2-isopropyl-6-[2-(1,1,7,7-tetramethyl-julolidin-9-yl)ethenyl]-4H-py ran (abbreviation: DCJTI), magnesium phthalocyanine, magnesium porphyrin, or phthalocyanine, or the like is preferable.

Note that the first electrode 101 and the second electrode 103 described in this embodiment may have structures similar to those of the first electrode and the second electrode described in Embodiment 2, respectively.

Further, the hole-injection layer 111, the hole-transport layer 112, the electron-transport layer 114, and the electron-injection layer 115 are provided as illustrated in FIG. 1 in this embodiment, and as for structures of these layers, the structures of the respective layers described in Embodiment 2 may be applied. However, these layers are not necessarily provided and may be provided according to element characteristics.

The above-described light-emitting element can emit light with high efficiency by use of the organometallic complex which is one embodiment of the present invention as a sensitizer.

Note that the structure described in this embodiment can be combined with any of the structures described in Embodiments 1 to 4 as appropriate.

(Embodiment 6)

In this embodiment, as one embodiment of the present invention, a passive matrix light-emitting device and an active matrix light-emitting device each of which is a light-emitting device manufactured using a light-emitting element will be described.

FIGS. 4A to 4D and FIG. 5 illustrate examples of passive matrix light-emitting devices.

In a passive-matrix (also referred to as "simple-matrix") light-emitting device, a plurality of anodes arranged in stripes (in stripe form) are provided to be perpendicular to a plurality of cathodes arranged in stripes, and a light-emitting layer is interposed at each intersection. Thus, a pixel at an intersection of an anode selected (to which a voltage is applied) and a cathode selected emits light.

Figure 4A:
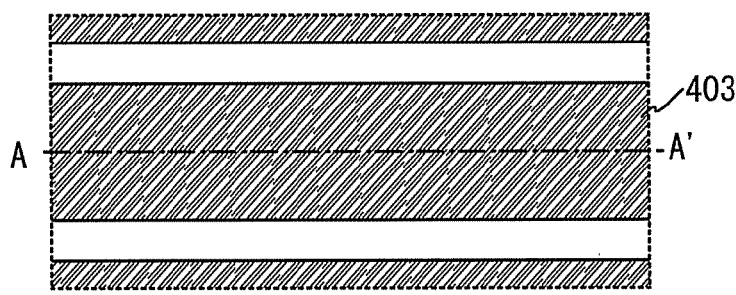
FIGS. 4A to 4D are views illustrating a passive matrix light-emitting device.
Figure 4B:
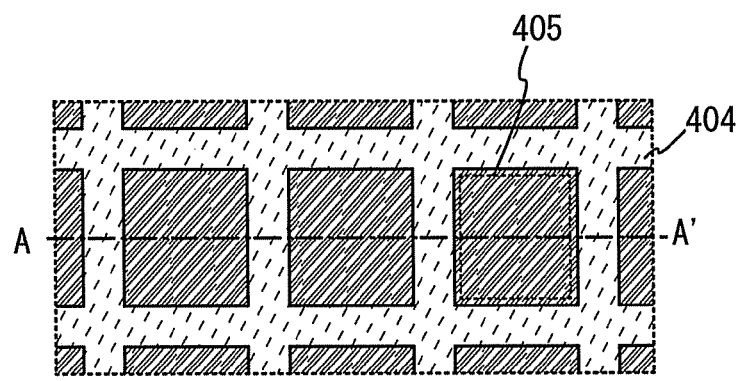
Figure 4C:
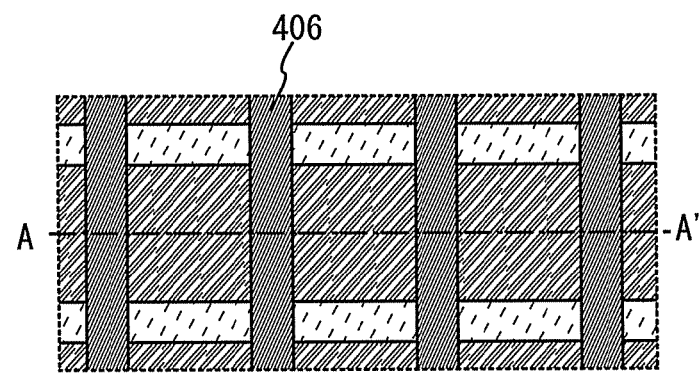
Figure 4D:
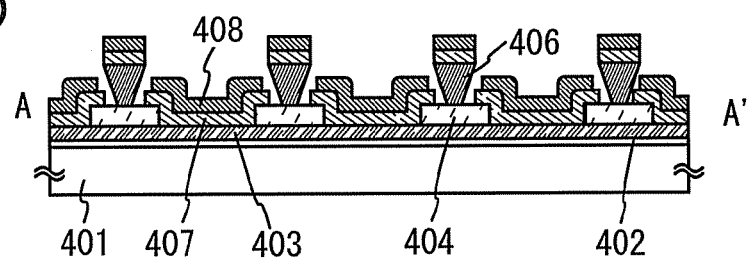

FIGS. 4A to 4C are top views illustrating a pixel portion before sealing. FIG. 4D is a cross-sectional view taken along the chain line A-A' in FIGS. 4A to 4C.

An insulating layer 402 is formed as a base insulating layer over a substrate 401. Note that the insulating layer 402 is not necessarily formed if the base insulating layer is not needed. A plurality of first electrodes 403 are arranged in stripes at regular intervals over the insulating layer 402 (see FIG. 4A).

In addition, a partition wall 404 having openings each corresponding to a pixel is provided over the first electrodes 403. The partition wall 404 having the openings is formed of an insulating material (a photosensitive or nonphotosensitive organic material (e.g., polyimide, acrylic, polyamide, polyimide amide, resist, or benzocyclobutene) or an SOG film (e.g., a $SiO_x$ film containing an alkyl group). Note that the openings each corresponding to a pixel serve as light-emitting regions (see FIG. 4B).

A plurality of inversely-tapered partition walls 406 parallel to each other are provided over the partition wall 404 having the openings to intersect with the first electrodes 403 (see FIG. 4C). The inversely-tapered partition walls 406 are formed by a photolithography method using a positive-type photosensitive resin, portion of which unexposed to light remains as a pattern, and by adjustment of the amount of light exposure or the length of development time so that a lower portion of a pattern is etched more.

After the inversely-tapered partition walls 406 are formed as illustrated in FIG. 4C, EL layers 407 and second electrodes 408 are sequentially formed as illustrated in FIG. 4D. The total thickness of the partition wall 404 having the openings and the inversely-tapered partition wall 406 is set to be larger than the total thickness of the EL layer 407 and the second electrode 408; thus, as illustrated in FIG. 4D, EL layers 407 and second electrodes 408 which are separated for plural regions are formed. Note that the plurality of separated regions are electrically isolated from one another.

The second electrodes 408 are electrodes in stripe form that are parallel to each other and extend along a direction intersecting with the first electrodes 403. Note that a plurality of stacked layers each including the EL layer 407 and part of conductive layer forming the second electrode 408 are also formed over the inversely-tapered partition walls 406; however, they are separated from the EL layer 407 and the second electrode 408.

Note that there is no particular limitation on the first electrode 403 and the second electrode 408 in this embodiment as long as one of them is an anode and the other is a cathode. Note that a stacked structure in which the EL layer 407 is included may be adjusted as appropriate in accordance with the polarity of the electrode.

Further, if necessary, a sealing material such as a sealing can or a glass substrate may be attached to the substrate 401 for sealing with an adhesive such as a sealant, so that the light-emitting element is placed in the sealed space. This can prevents deterioration of the light-emitting element. Note that the sealed space may be filled with a filler or a dry inert gas. Furthermore, a desiccant or the like may be put between the substrate and the sealant in order to prevent deterioration of the light-emitting element due to moisture. The desiccant removes a minute amount of moisture, thereby achieving sufficient desiccation. The desiccant may be a substance which absorbs moisture by chemical adsorption, such as an oxide of an alkaline earth metal as typified by calcium oxide or barium oxide. Alternatively, the desiccant may be a substance which adsorbs moisture by physical adsorption such as zeolite or silica gel.

Figure 5:
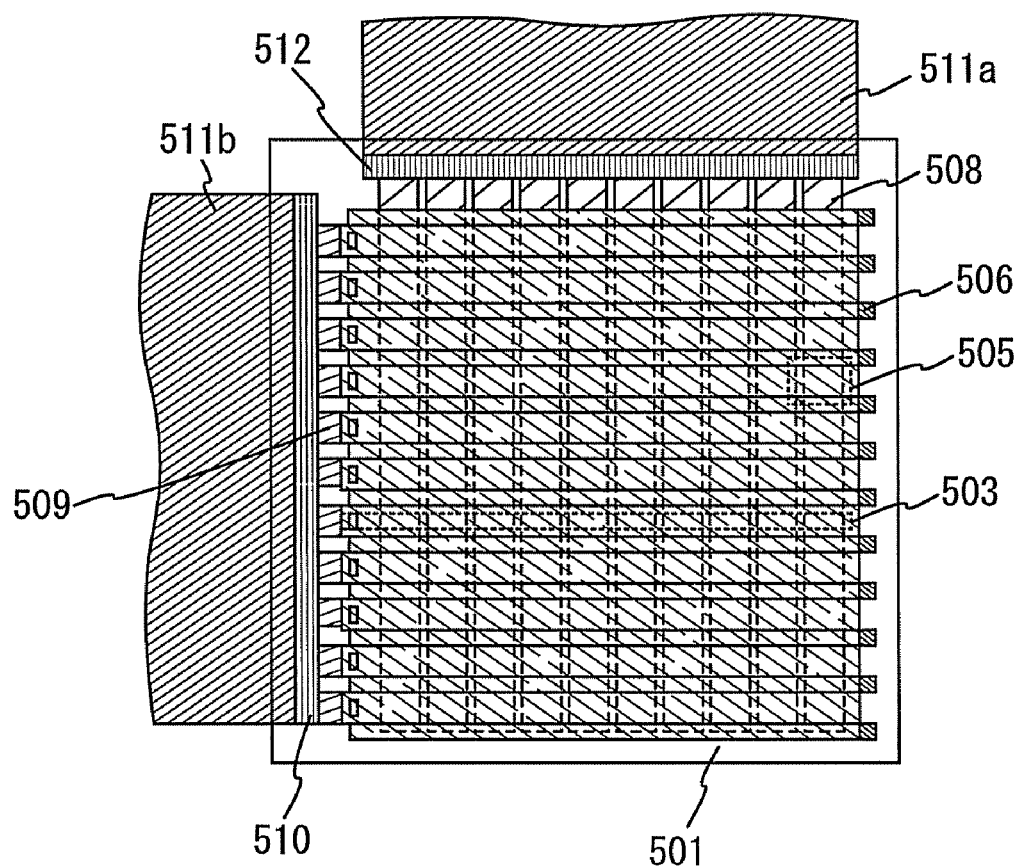
FIG. 5 illustrates a passive matrix light-emitting device.

FIG. 5 is a top view of the case where the passive matrix light-emitting device illustrated in FIGS. 4A to 4D is mounted with an FPC and the like.

In FIG. 5, scan lines and data lines are perpendicularly intersect with each other in a pixel portion for displaying images.

Here, the first electrode 403, the second electrode 408, and the inversely-tapered partition wall 406 in FIGS. 4A to 4D correspond to a scan line 503, a data line 508, and a partition wall 506 in FIG. 5, respectively. The EL layers 407 in FIGS. 4A to 4D are interposed between the data lines 508 and the scan lines 503, and an intersection portion indicated by a region 505 corresponds to one pixel.

Note that the scan lines 503 are electrically connected at their ends to connection wirings 509, and the connection wirings 509 are connected to an FPC 511b through an input terminal 510. In addition, the data lines are connected to an FPC 511a through the input terminal 512.

If necessary, a polarizing plate, a circularly polarizing plate (including an elliptically polarizing plate), a retardation plate (a quarter-wave plate or a half-wave plate), or an optical film such as a color filter may be provided as appropriate over a light-emitting surface. Further, the polarizing plate or the circularly polarizing plate may be provided with an anti-reflection film. For example, anti-glare treatment may be carried out by which reflected light can be diffused by projections and depressions on the surface so as to deep reduce the glare.

Note that, although FIG. 5 illustrates an example in which a driver circuit is not provided over the substrate, an IC chip including a driver circuit may be mounted on the substrate.

Further, in the case where the IC chip is mounted, a data line side IC and a scan line side IC, in each of which the driver circuit for transmitting a signal to a pixel portion is formed, are mounted on the periphery of (outside) the pixel portion by a COG method. The mounting may be performed using TCP or a wire bonding method other than the COG method. TCP is a TAB tape mounted with an IC, and a TAB tape is connected to a wiring over an element formation substrate and an IC is mounted. Each of the data line side IC and the scanning line side IC may be formed using a silicon substrate, or may be formed by formation of a driver circuit with a TFT over a glass substrate, a quartz substrate, or a plastic substrate.

Figure 6A:
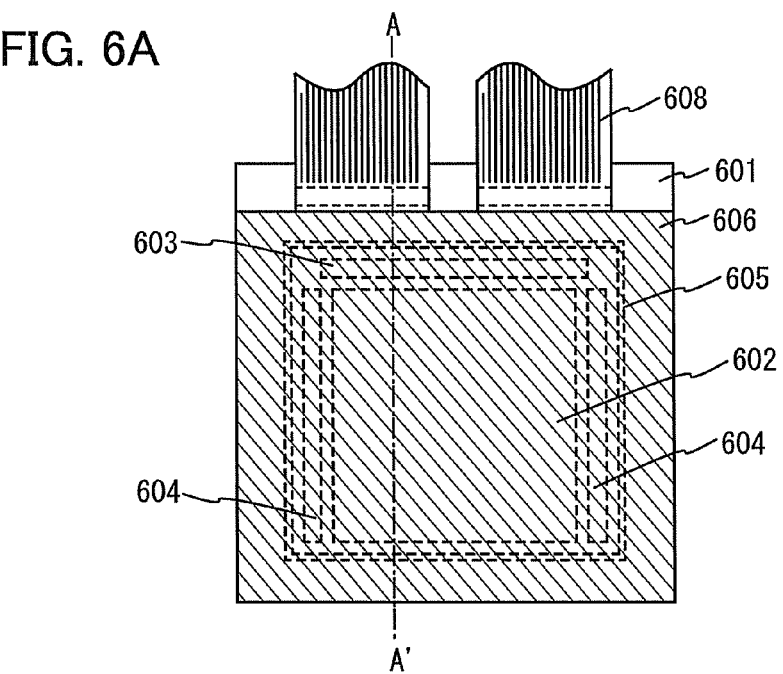
FIGS. 6A and 6B are views illustrating an active matrix light-emitting device.
Figure 6B:
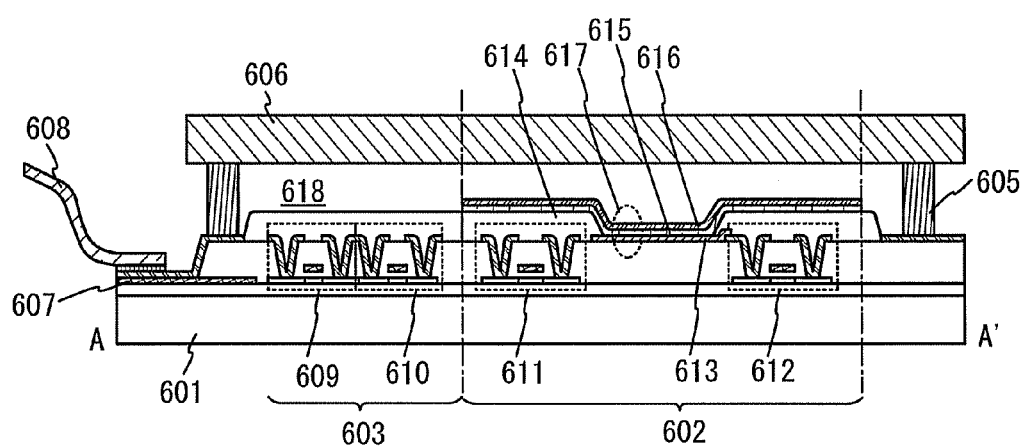

Next, an example of an active-matrix light-emitting device will be described with reference to FIGS. 6A and 6B. Note that FIG. 6A is a top view illustrating a light-emitting device and FIG. 6B is a cross-sectional view taken along the chain line A-A' in FIG. 6A. The active matrix light-emitting device according to this embodiment includes a pixel portion 602 provided over an element substrate 601, a driver circuit portion (a source side driver circuit) 603, and a driver circuit portion (a gate side driver circuit) 604. The pixel portion 602, the driver circuit portion 603, and the driver circuit portion 604 are sealed, with a sealing material 605, between the element substrate 601 and a sealing substrate 606.

In addition, over the element substrate 601, a lead wiring 607 for connecting an external input terminal, through which a signal (e.g., a video signal, a clock signal, a start signal, a reset signal, or the like) or an electric potential is transmitted to the driver circuit portion 603 and the driver circuit portion 604, is provided. Here, an example is described in which a flexible printed circuit (FPC) 608 is provided as the external input terminal. Although only an FPC is shown here, this FPC may have a printed wiring board (PWB) attached. The light-emitting device in this specification includes not only a light-emitting device itself but also a light-emitting device with an FPC or a PWB attached.

Next, a cross-sectional structure will be described with reference to FIG. 6B. The driver circuit portion and the pixel portion are formed over the element substrate 601, and in FIG. 6B, the driver circuit portion 603 that is a source side driver circuit and the pixel portion 602 are illustrated.

An example is illustrated in which a CMOS circuit which is a combination of an n-channel TFT 609 and a p-channel TFT 610 is formed as the driver circuit portion 603. Note that a circuit included in the driver circuit portion may be formed using various types of circuits such as CMOS circuits, PMOS circuits, or NMOS circuits. Although a driver integrated type in which the driver circuit is formed over the substrate is described in this embodiment, the driver circuit may not necessarily be formed over the substrate, and the driver circuit can be formed outside, not over the substrate.

The pixel portion 602 is formed of a plurality of pixels each of which includes a switching TFT 611, a current control TFT 612, and an anode 613 which is electrically connected to a wiring (a source electrode or a drain electrode) of the current control TFT 612. Note that an insulator 614 is formed to cover end portions of the anode 613. In this embodiment, the insulator 614 is formed using a positive photosensitive acrylic resin.

The insulator 614 is preferably formed so as to have a curved surface with curvature at an upper end portion or a lower end portion thereof in order to obtain favorable coverage by a film which is to be stacked over the insulator 614. For example, in the case of using a positive photosensitive acrylic resin as a material for the insulator 614, the insulator 614 is preferably formed so as to have a curved surface with a curvature radius (0.2 μm to 3 μm) at the upper edge portion. Note that either a negative photosensitive material that becomes insoluble in an etchant by light irradiation or a positive photosensitive material that becomes soluble in an etchant by light irradiation can be used for the insulator 614. As the insulator 614, without limitation to an organic compound, either an organic compound or an inorganic compound such as silicon oxide or silicon oxynitride can be used.

An EL layer 615 and a cathode 616 are stacked over the anode 613. Note that when an ITO film is used as the anode 613, and a stacked film of a titanium nitride film and a film containing aluminum as its main component or a stacked film of a titanium nitride film, a film containing aluminum as its main component, and a titanium nitride film is used as the wiring of the current controlling TFT 612 which is connected to the anode 613, resistance of the wiring is low and favorable ohmic contact with the ITO film can be obtained. Note that, although not illustrated, the cathode 616 is electrically connected to an FPC 608 which is an external input terminal.

Note that in the EL layer 615, at least a light-emitting layer is provided, and in addition to the light-emitting layer, a hole-injection layer, a hole-transport layer, an electron-transport layer, or an electron-injection layer is provided as appropriate. A light-emitting element 617 is formed of a stacked structure of the anode 613, the EL layer 615, and the cathode 616.

Although the cross-sectional view of FIG. 6B illustrates only one light-emitting element 617, a plurality of light-emitting elements are arranged in matrix in the pixel portion 602. Light-emitting elements which provide three kinds of emissions (R, G, and B) are selectively formed in the pixel portion 602, whereby a light-emitting device capable of full color display can be formed. Alternatively, a light-emitting device which is capable of full color display may be manufactured by a combination with color filters.

Further, the sealing substrate 606 is attached to the element substrate 601 with the sealing material 605, whereby a light-emitting element 617 is provided in a space 618 surrounded by the element substrate 601, the sealing substrate 606, and the sealing material 605. The space 618 may be filled with an inert gas (such as nitrogen or argon), or the sealing material 605.

Note that an epoxy-based resin is preferably used as the sealing material 605. Such a material preferably allows as little moisture and oxygen as possible to penetrate. As the sealing substrate 606, a plastic substrate formed of FRP (fiberglass-reinforced plastics), PVF (polyvinyl fluoride), a polyester film; polyester or acrylic; or the like can be used instead of a glass substrate or a quartz substrate.

In this way, an active matrix light-emitting device can be obtained.

Note that the structure described in Embodiment 6 can be combined with any of the structures described in Embodiments 1 to 5 as appropriate.

(Embodiment 7)

In this embodiment, examples of various electronic devices and lighting devices, which are completed using the light-emitting device of one embodiment of the present invention, will be described with reference to FIGS. 7A to 7E and FIG. 8.

As the electronic devices to which the light-emitting device is applied, for example, there are a television device (also referred to as TV or a television receiver), a monitor for a computer or the like, a camera such as a digital camera, a digital video camera, a digital photo frame, a cellular phone (also referred to as a cellular phone or a portable telephone device), a portable game machine, a portable information terminal, an audio playback device, and a large game machine such as a pin-ball machine. Specific examples of these electronic devices and lighting device are illustrated in FIGS. 7A to 7E.

Figure 7A:
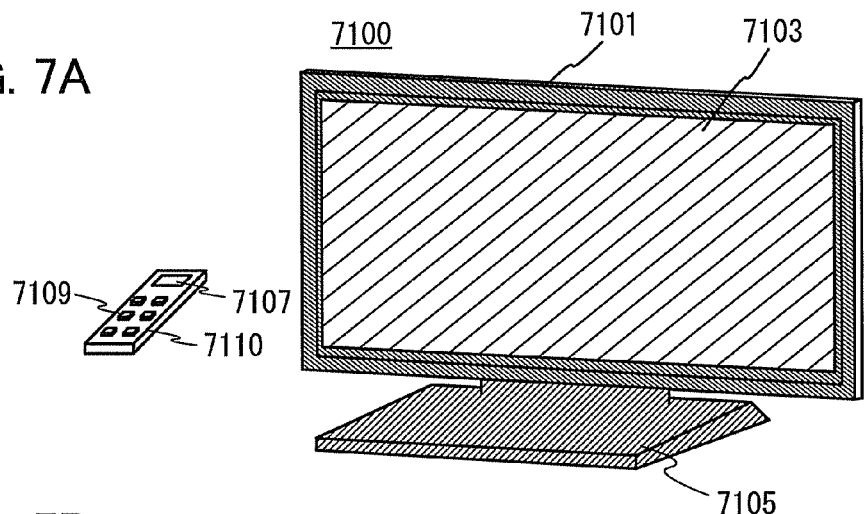
FIGS. 7A to 7E illustrate illustrating electronic devices.

FIG. 7A illustrates an example of a television device 7100. In the television device 7100, a display portion 7103 is incorporated in a housing 7101. Images can be displayed by the display portion 7103, and the light-emitting device can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, general television broadcasting can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 7B:
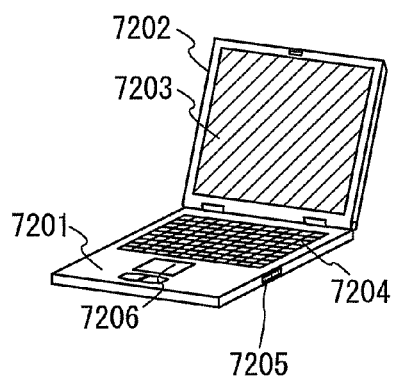

FIG. 7B illustrates a computer, which includes a main body 7201, a housing 7202, a display portion 7203, a keyboard 7204, an external connecting port 7205, a pointing device 7206, and the like. This computer is manufactured by using a light-emitting device for the display portion 7203.

Figure 7C:
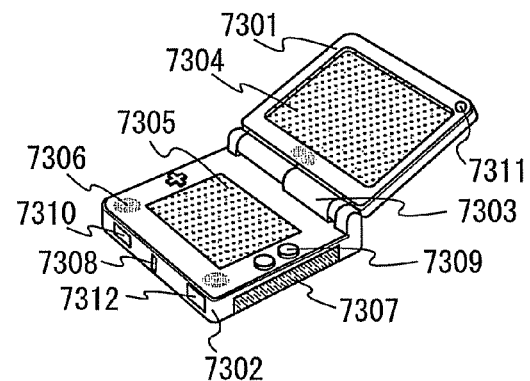

FIG. 7C illustrates a portable game machine, which includes two housings, a housing 7301 and a housing 7302, which are connected with a joint portion 7303 so that the portable game machine can be opened or folded. A display portion 7304 is incorporated in the housing 7301 and a display portion 7305 is incorporated in the housing 7302. In addition, the portable game machine illustrated in FIG. 7C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. It is needless to say that the structure of the portable games machine is not limited to the above as long as the light-emitting device is used for at least either the display portion 7304 or the display portion 7305, or both. The portable game machine illustrated in FIG. 7C has a function of reading out a program or data stored in a storage medium to display it on the display portion, and a function of sharing information with another portable game machine by wireless communication. The portable game machine illustrated in FIG. 7C can have a variety of functions without limitation to the above.

Figure 7D:
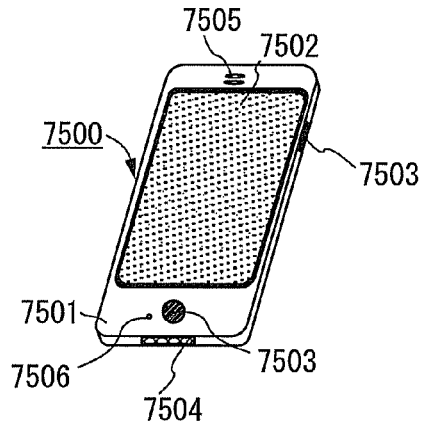

FIG. 7D illustrates an example of a cellular phone. The cellular phone 7400 is provided with a display portion 7402 incorporated in a housing 7401, operation buttons 7403, an external connection port 7404, a speaker 7405, a microphone 7406, and the like. Note that the cellular phone 7400 is manufactured using a light-emitting device for the display portion 7402.

When the display portion 7402 of the cellular phone 7400 illustrated in FIG. 7D is touched with a finger or the like, data can be input into the cellular phone 7400. Further, operations such as making calls and composing e-mails can be performed by touching the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are mixed.

For example, in the case of making a call or composing an e-mail, a text input mode mainly for inputting text is selected for the display portion 7402 so that text displayed on a screen can be inputted. In that case, it is preferable to display a keyboard or number buttons on almost all the area of the screen of the display portion 7402.

When a detection device including a sensor for detecting inclination, such as a gyroscope or an acceleration sensor, is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are switched by touching the display portion 7402 or operating the operation buttons 7403 of the housing 7401. Alternatively, the screen modes can be switched depending on kinds of images displayed on the display portion 7402. For example, when a signal for an image displayed in the display portion is data of moving images, the screen mode is switched to the display mode. When the signal is text data, the screen mode is switched to the input mode.

Moreover, in the input mode, when input by touching the display portion 7402 is not performed within a specified period while a signal detected by an optical sensor in the display portion 7402 is detected, the screen mode may be controlled so as to be switched from the input mode to the display mode.

The display portion 7402 can function as an image sensor. For example, an image of a palm print, a fingerprint, or the like is taken by touching the display portion 7402 with the palm or the finger, whereby personal authentication can be performed. Furthermore, by provision of a backlight or a sensing light source emitting a near-infrared light for the display portion, an image of a finger vein, a palm vein, or the like can also be taken.

Figure 7E:
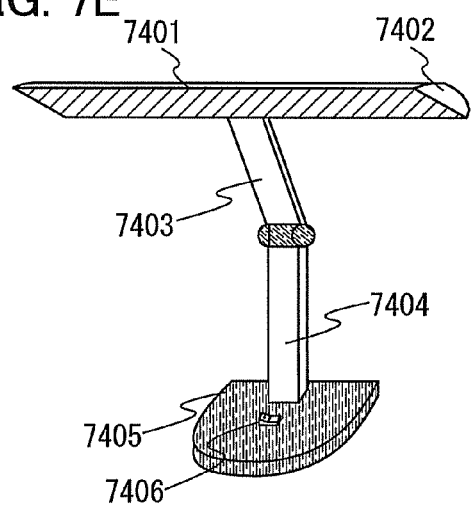

FIG. 7E illustrates a desk lamp, which includes a lighting portion 7501, a lampshade 7502, an adjustable arm 7503, a support 7504, a base 7505, and a power supply 7506. The desk lamp is manufactured using a light-emitting device for the lighting portion 7501. Note that the lighting device includes a ceiling light, a wall light, and the like in its category.

Figure 8:
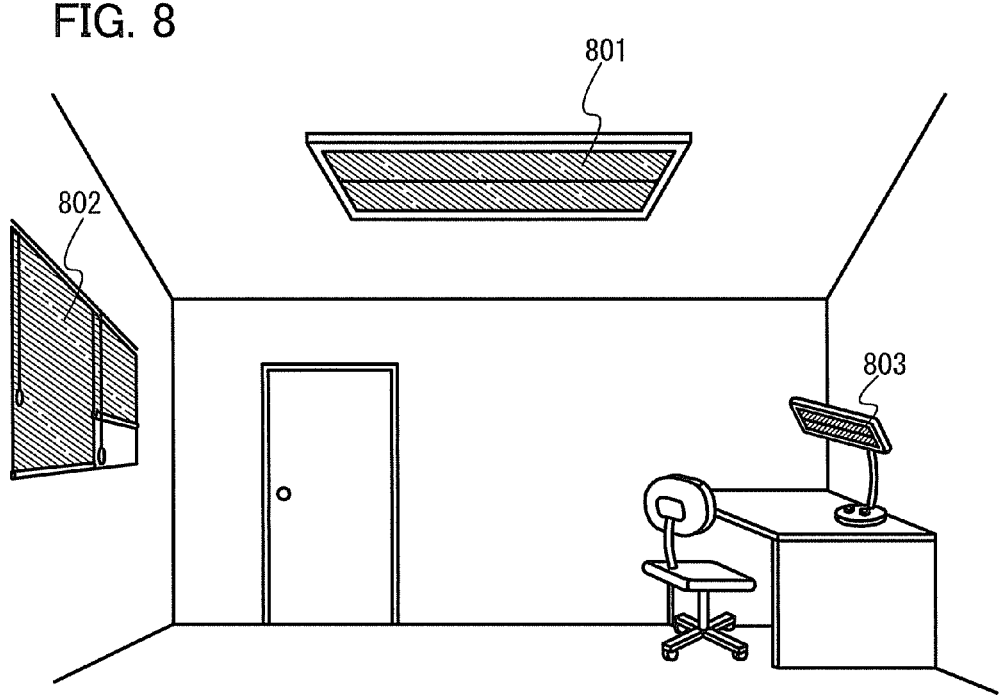
FIG. 8 illustrates lighting devices.

FIG. 8 illustrates an example in which the light-emitting device is used for an indoor lighting device 801. Since the light-emitting device can have a larger area, the light-emitting device can be used as a lighting device having a large area. Alternatively, the light-emitting device can be used as a roll-type lighting device 802. Note that as illustrated in FIG. 8, a desk lamp 803 described with reference to FIG. 7E may be used together in a room provided with the indoor lighting device 801.

As described above, electronic devices and a lighting device can be obtained by application of the light-emitting device. Application range of the light-emitting device is so wide that the light-emitting device can be applied to electronic devices in a variety of fields.

Note that the structure described in this embodiment can be combined with any of the structures described in Embodiments 1 to 6 as appropriate.

EXAMPLE 1

Synthesis Example

This example shows a synthesis method of (acetylacetonato)bis[2-(1-naphthyl)-3,5-dimethylpyrazinato]iridium(III) (abbreviation: [Ir(dm1npr)$_2$(acac)]), which is the organometallic complex of one embodiment of the present invention represented by Structural Formula (100) in Embodiment 1. A structure of [Ir(dm1npr)$_2$(acac)] is shown below.

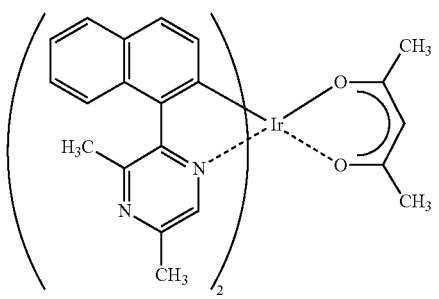

(100)

Step 1: Synthesis of 2-(1-naphthyl)-3,5-dimethylpyrazine (abbreviation: Hdm1npr)

First, into a recovery flask equipped with a reflux pipe were put 2.05 g of 2-chloro-3,5-dimethylpyrazine, 2.48 g of 1-naphthylboronic acid, 1.53 g of sodium carbonate, 0.066 g of bis(triphenylphosphine)palladium(II)dichloride (abbreviation: Pd(PPh$_3$)$_2$Cl$_2$), 15 mL of water, and 15 mL of acetonitrile, and the air in the flask was replaced with argon. This reaction container was subjected to irradiation with microwaves (2.45 GHz, 100 W) for 10 minutes, whereby heating was performed. After that, water was added to this solution, and an organic layer was extracted with dichloromethane. The obtained organic layer was washed with water and dried with magnesium sulfate. After the drying, the solution was filtered. The solvent of this solution was distilled off, and then the obtained residue was purified by silica gel column chromatography using dichloromethane as a developing solvent. Accordingly, Hdm1npr (a light orange powder, 59% yield), which was the substance to be produced, was obtained. Note that the irradiation with microwaves was performed using a microwaves synthesis system (Discover, produced by CEM Corporation). The synthesis scheme of Step 1 is shown in (a-1) below.

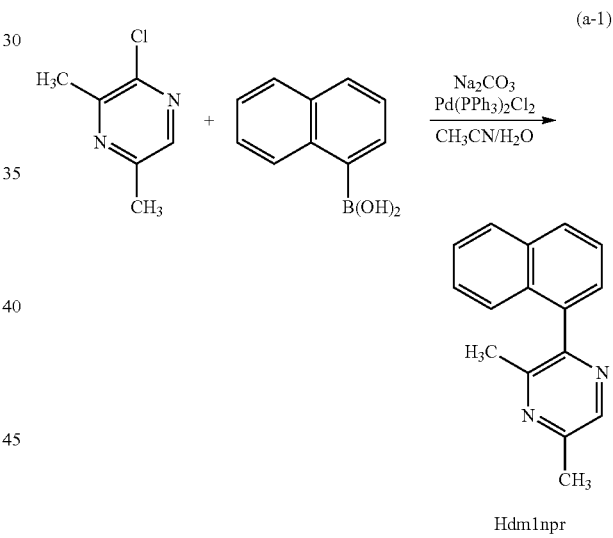

(a-1)

Step 2: Synthesis of di-μ-chloro-bis[bis{2-(1-naphthyl)-3,5-dimethylpyrazine}iridium(III)] (abbreviation: [Ir(dm1npr)$_2$Cl]$_2$)

Next, into a recovery flask equipped with a reflux pipe were put 15 mL of 2-ethoxyethanol, 5 mL of water, 1.99 g of Hdm1npr obtained in above Step 1, and 1.27 g of iridium chloride hydrate (IrCl$_3$.H$_2$O) (produced by Sigma-Aldrich Corporation), and the air in the flask was replaced with argon. After that, irradiation with microwaves (2.45 GHz, 100 W) was performed for 1 hour to cause a reaction. The reaction solution was filtered, and then the filtrate was concentrated and dried. The obtained residue was recrystallized from ethanol, whereby a dinuclear complex [Ir(dm1npr)$_2$Cl]$_2$ was obtained (a dark orange powder, 54% yield). Further, the synthesis scheme of Step 2 is shown in (b-2) below.

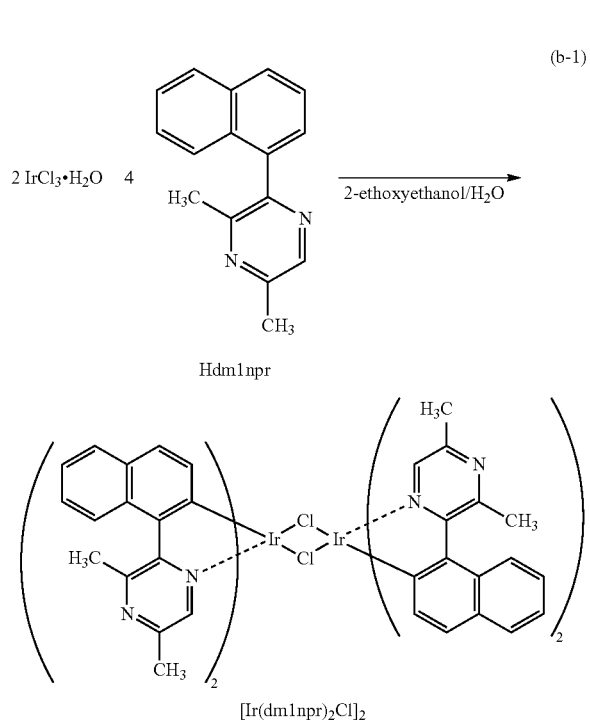

(b-1)

Hdm1npr

[Ir(dm1npr)₂Cl]₂

Step 3: Synthesis of (acetylacetonato)bis[2-(1-naphthyl)-3,5-dimethylpyrazinato]iridium(III) (abbreviation: [Ir(dm1npr)₂(acac)])

Furthermore, into a recovery flask equipped with a reflux pipe were put 20 mL of 2-ethoxyethanol, 1.60 g of the dinuclear complex [Ir(dm1npr)₂Cl]₂ obtained in above Step 2, 0.36 mL of acetylacetone, and 1.22 g of sodium carbonate, and the air in the flask was replaced with argon. After that, irradiation with microwaves (2.45 GHz, 100 W) was performed for 30 minutes to cause a reaction. The reaction solution was filtered. The obtained solid was dissolved in dichloromethane. The solution was filtered to remove the insoluble portion, and then recrystallized from a mixed solvent of methanol and dichloromethane. Accordingly, a dark orange powder of the organometallic complex [Ir(dm1npr)₂(acac)], which is one embodiment of the present invention, was obtained (45% yield). The synthesis scheme of Step 3 is shown in (c-3) below.

(c-1)

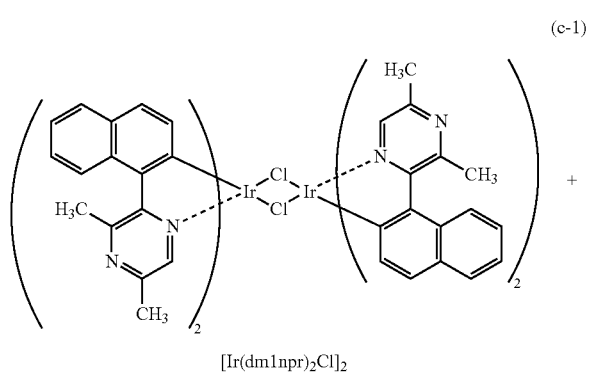

[Ir(dm1npr)₂Cl]₂

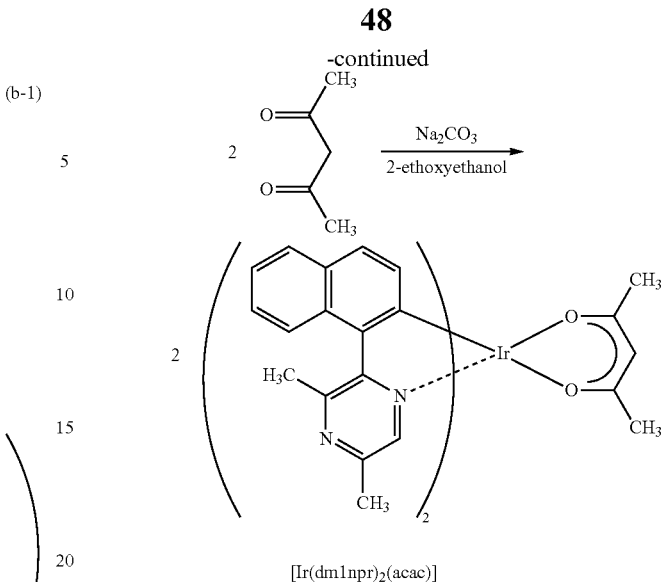

[Ir(dm1npr)₂(acac)]

Figure 9:
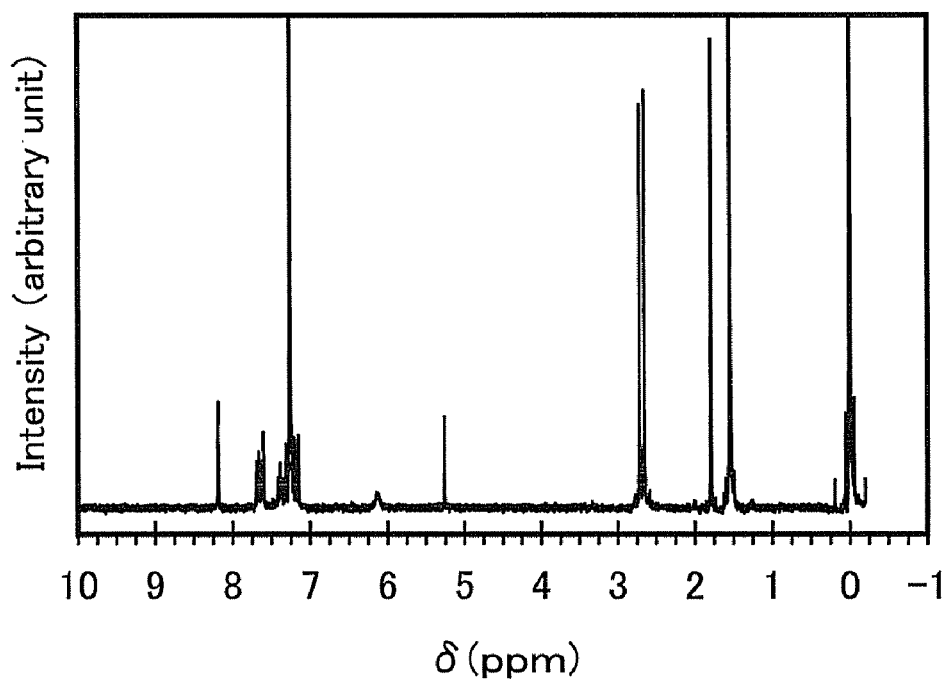
FIG. 9 shows a $^1$H NMR chart of an organometallic complex represented by Structural Formula (100).

Results of analysis of the dark orange powder obtained in above Step 3 by nuclear magnetic resonance spectrometry (¹H NMR) are shown below. In addition, FIG. 9 is a ¹H NMR chart. According to the results, it was found that the organometallic complex [Ir(dm1npr)₂(acac)], which is one embodiment of the present invention and represented by Structural Formula (100) above, was obtained in this example.

¹H NMR. δ (CDCl₃): 1.79(s, 6H), 2.66(s, 6H), 2.72(s, 6H), 5.26(s, 1H), 6.15(brm, 2H), 7.17(d, 2H), 7.24(m, 2H), 7.39(t, 2H), 7.65(m, 4H), 8.19(s, 2H).

Figure 10:
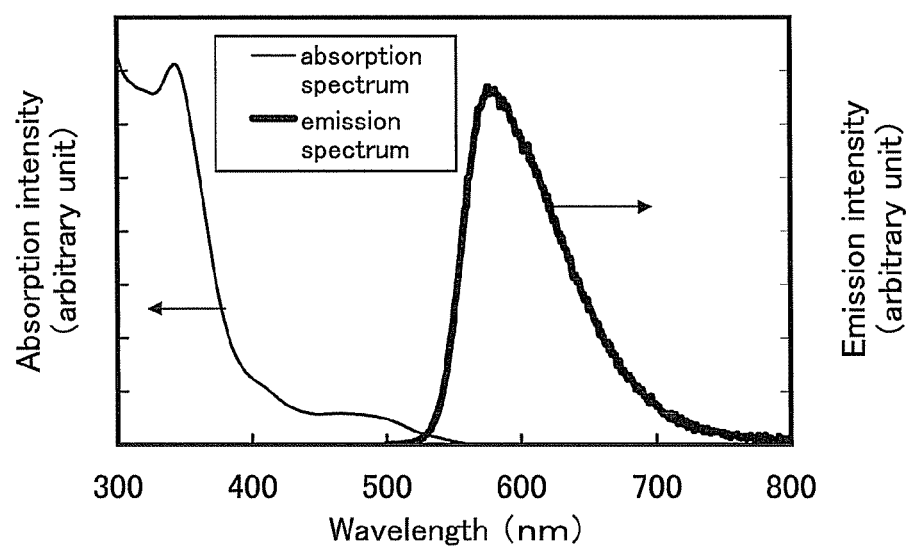
FIG. 10 shows an ultraviolet-visible absorption spectrum and an emission spectrum of the organometallic complex represented by Structural Formula (100).

Next, [Ir(dm1npr)₂(acac)] was analyzed by an ultraviolet-visible (UV) absorption spectroscopy. The UV spectrum was measured using an ultraviolet-visible spectrophotometer (V550, produced by JASCO Corporation) at room temperature by use of a dichloromethane solution (0.076 mmol/L). In addition, an emission spectrum of [Ir(dm1npr)₂(acac)] was measured. The emission spectrum was measured by a fluorescence spectrophotometer (FS920, produced by Hamamatsu Photonics Corporation) using a degassed dichloromethane solution (0.27 mmol/L) at room temperature. FIG. 10 shows the measurement results. The horizontal axis indicates wavelength, and the vertical axis indicates absorption intensity and the emission intensity.

As shown in FIG. 10, the organometallic complex [Ir(dm1npr)₂(acac)] which is one embodiment of the present invention has a peak of emission at 680 nm, and deep red light was observed from the dichloromethane solution.

EXAMPLE 2

Figure 11:
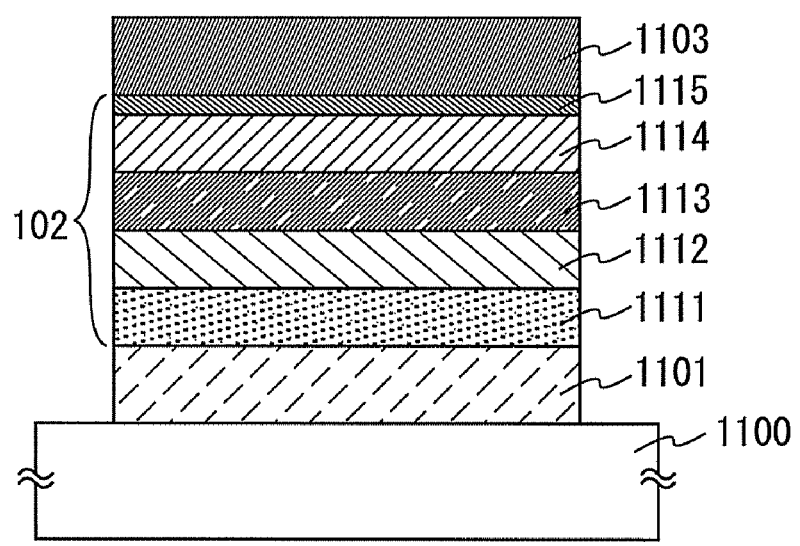
FIG. 11 illustrates a light-emitting element which is one embodiment of the present invention.

A light-emitting element (Light-emitting Element 2) will be described in which the organometallic complex [Ir(dm1npr)₂(acac)] (Structural Formula (100)), which is one embodiment of the present invention and synthesized in Example 1, is used as a light-emitting substance. Further, as a reference light-emitting element, a light-emitting element (Light-emitting Element 1) will also be described in which a light-emitting substance represented by Structural Formula (i) below is used as a light-emitting substance. Note that structures of other organic compounds used in this example are represented by Structural Formulas (ii) to (v). In addition, element structures of the light-emitting elements will be described on the basis of FIG. 11.

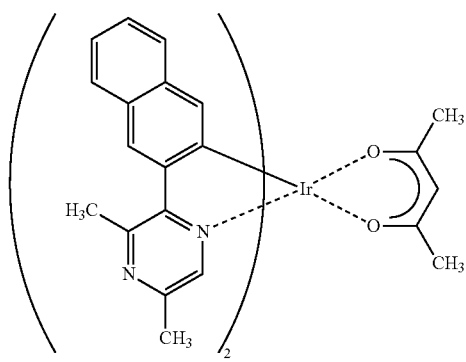

[Ir(dm2npr)₂(acac)]

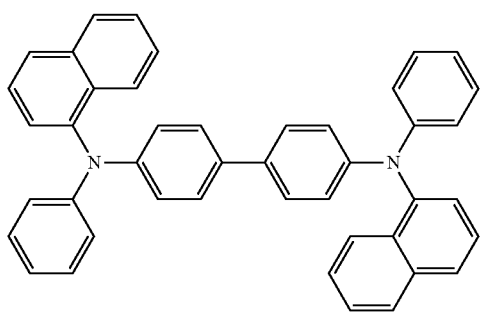

NPB

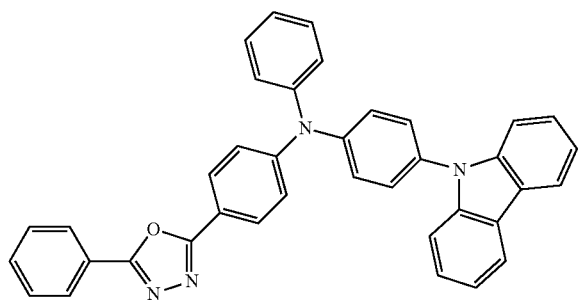

YGAO11

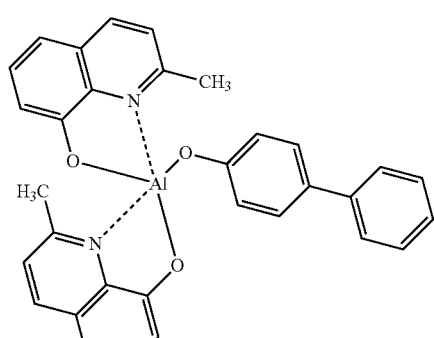

BAlq

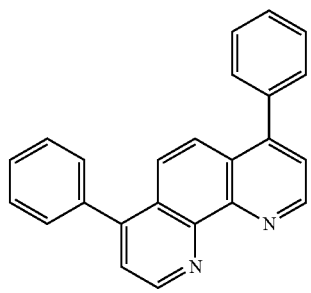

Bphen

<<Manufacture of Light-Emitting Elements 1 and 2>>

First, as a first electrode 1101, indium tin oxide containing silicon oxide (ITSO) is formed to a thickness of 110 nm over a substrate 1100 made of glass. Note that the periphery of the ITSO is covered with an insulating film so that a surface of the ITSO of 2 mm×2 mm is exposed. Here, the first electrode 1101 is an electrode that functions as an anode of the light-emitting element.

Next, as pretreatment for forming the light-emitting element over the substrate 1100, the surface of the substrate was washed, baked at 200° C. for one hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 over which the first electrode 1101 was formed faced downward. In this example, a hole-injection layer 1111, a hole-transport layer 1112, a light-emitting layer 1113, an electron-transport layer 1114, and an electron-injection layer 1115 which are included in an EL layer 1102 are sequentially formed.

After reducing the pressure of the vacuum evaporation apparatus to $10^{-4}$ Pa, NPB represented by the above Structural Formula (ii) and molybdenum(VI) oxide were co-evaporated with a mass ratio of NPB to molybdenum(VI) oxide being 4:1, whereby the hole-injection layer 1111 was formed. The thickness of the hole-injection layer 1111 was 50 nm. Note that the co-evaporation is an evaporation method in which some different substances are evaporated from some different evaporation sources at the same time.

Next, NPB was evaporated to a thickness of 10 nm as the hole-transport layer 1112.

Next, the light-emitting layer 1113 was formed over the hole-transport layer 1112. In the case of Light-emitting Element 1, YGAO11 represented by the above Structural Formula (iii) and [Ir(dm2npr)₂(acac)] represented by the above Structural Formula (i) were co-evaporated over the hole-transport layer 1112 with a mass ratio of YGAO11 to [Ir(dm2npr)₂(acac)] being 1:0.025 so that the light-emitting layer 1113 was formed. In the case of Light-emitting Element 2, YGAO11 and [Ir(dm1npr)₂(acac)] represented by the above Structural Formula (100) were co-evaporated over the hole-transport layer 1112 with a mass ratio of YGAO11 to [Ir(dm1npr)₂(acac)] being 1:0.025 so that the light-emitting layer 1113 was formed. The thickness of the light-emitting layer 1113 in each element was 30 nm.

Next, after evaporating BAlq represented by the above Structural Formula (iv) to a thickness of 10 nm, BPhen represented by the above Structural Formula (v) was further evaporated to a thickness of 40 nm, whereby the electron-transport layer 1114 was formed. Furthermore, lithium fluoride was evaporated to a thickness of 2 nm over the electron-transport layer 1114, whereby the electron-injection layer 1115 was formed.

Next, aluminum was deposited to a thickness of 200 nm as a second electrode 1103. Thus, the light-emitting elements (Light-emitting Elements 1 and 2) each of which is one embodiment of the present invention were obtained. Note that the second electrode 1103 is an electrode that functions as a cathode. In the above evaporation steps, evaporation was all performed by a resistance heating method.

Further, these light-emitting elements were sealed in a glove box under a nitrogen atmosphere to prevent being exposed to the atmosphere.

<<Operation Characteristics of Light-Emitting Elements 1 and 2>>

Operation characteristics of each of the manufactured light-emitting elements (Light-emitting Elements 1 and 2) were measured. Note that the measurement was carried out at room temperature (under an atmosphere in which the temperature was kept at 25° C.).

Figure 12:
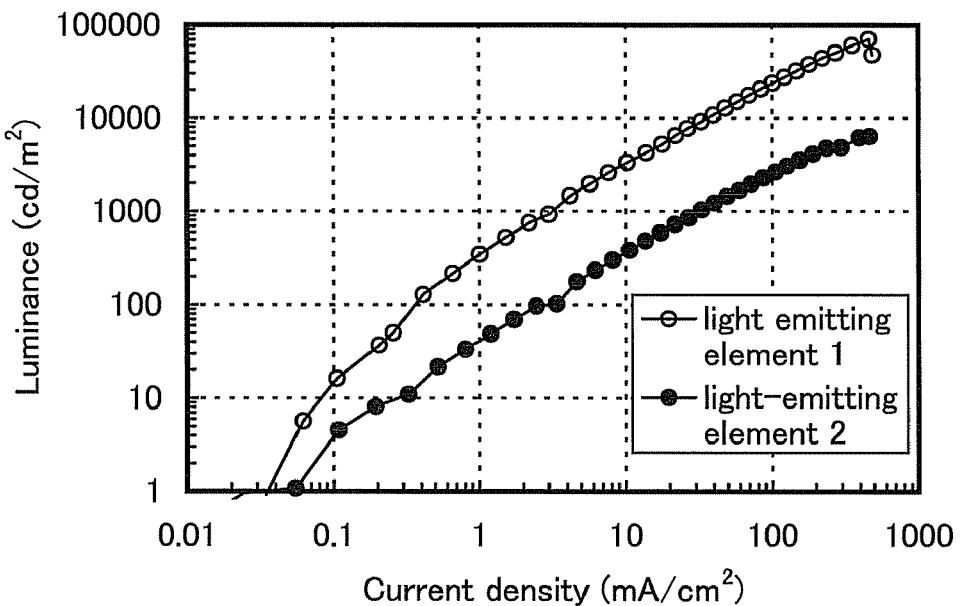
FIG. 12 shows current density-luminance characteristics of light-emitting elements each of which is one embodiment of the present invention.
Figure 13:
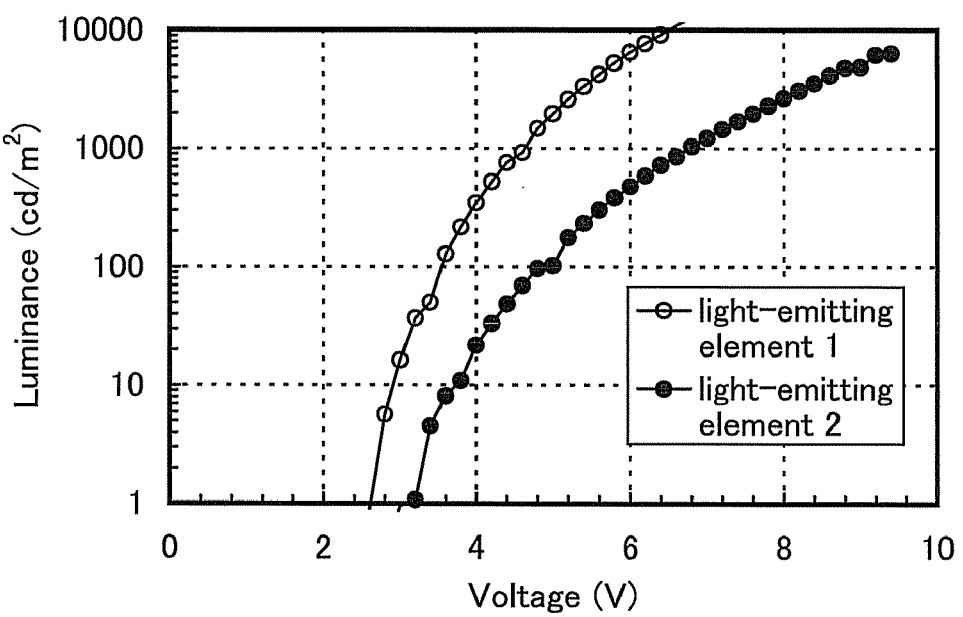
FIG. 13 shows voltage-luminance characteristics of the light-emitting elements each of which is one embodiment of the present invention.

FIG. 12 shows current density-luminance characteristics of each light-emitting element. In FIG. 12, the vertical axis represents luminance (cd/m$^2$) and the horizontal axis represents current density (mA/cm$^2$). FIG. 13 shows voltage-luminance characteristics of each light-emitting element. In FIG. 13, the vertical axis represents luminance (cd/m$^2$) and the horizontal axis represents voltage (V).

Figure 14:
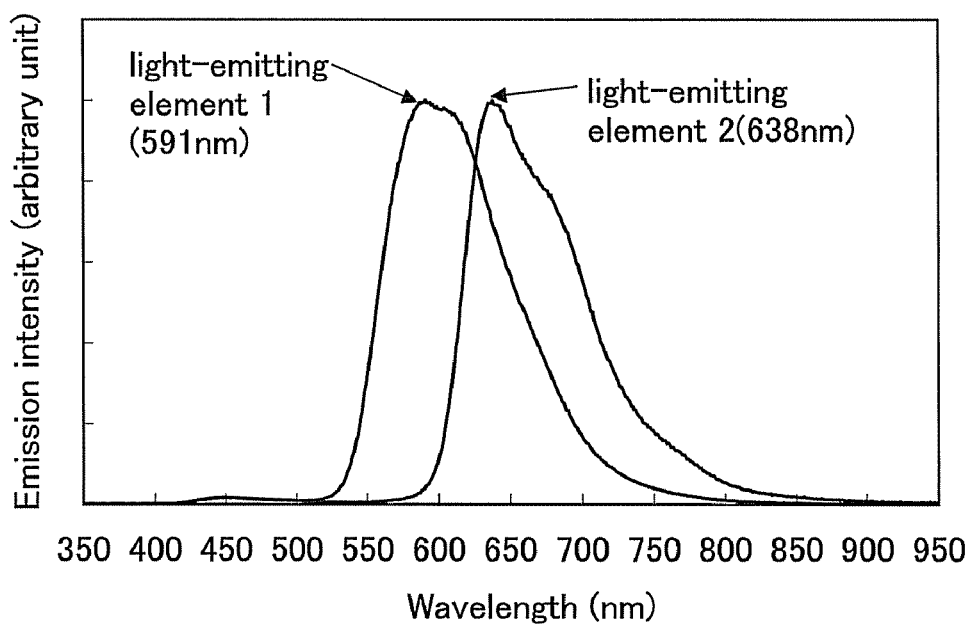
FIG. 14 shows emission spectra of the light-emitting elements each of which is one embodiment of the present invention.

FIG. 14 shows emission spectra obtained when the respective light-emitting elements were supplied with a current at a current density of 25 mA/cm$^2$. As shown in FIG. 14, Light-emitting Elements 1 and 2 have peaks of emission spectra at 591 nm and 638 nm, respectively, indicating that Light-emitting Element 2 exhibits red emission with higher color purity than Light-emitting Element 1 which exhibits orange emission. It was also found that the emission spectrum of Light-emitting Element 2 is derived from emission of the organometallic complex [Ir(dm1npr)$_2$(acac)] which is one embodiment of the present invention.

This application is based on Japanese Patent Application serial no. 2009-232961 filed with the Japan Patent Office on Oct. 7, 2009, the entire contents of which are hereby incorporated by reference.

What is claimed is:

1. An organometallic complex comprising a structure represented by General Formula (G1):

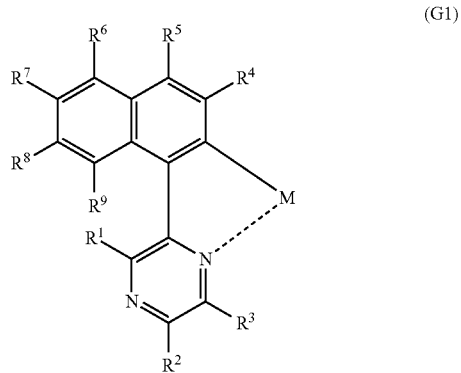

(G1)

wherein:
$R^1$ and $R^2$ individually represent any of an alkyl group having 1 to 4 carbon atoms, an alkoxy group having 1 to 4 carbon atoms, an alkylthio group having 1 to 4 carbon atoms, or an alkoxycarbonyl group having 1 to 5 carbon atoms;
$R^3$ represents hydrogen or an alkyl group having 1 to 4 carbon atoms;
$R^4$, $R^5$, $R^6$, $R^7$, $R^8$, and $R^9$ individually represent any of hydrogen, an alkyl group having 1 to 4 carbon atoms, an alkoxy group having 1 to 4 carbon atoms, a halogen group, a haloalkyl group having 1 to 4 carbon atoms, or an aryl group having 6 to 12 carbon atoms; and
M is a central metal and represents either a Group 9 element or a Group 10 element.

2. An organometallic complex comprising a structure represented by General Formula (G2):

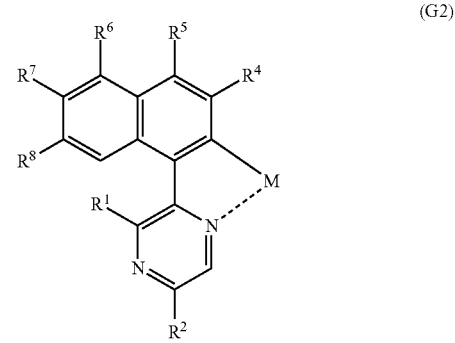

(G2)

wherein:
$R^1$ and $R^2$ individually represent any of an alkyl group having 1 to 4 carbon atoms, an alkoxy group having 1 to 4 carbon atoms, an alkylthio group having 1 to 4 carbon atoms, or an alkoxycarbonyl group having 1 to 5 carbon atoms;
$R^4$, $R^5$, $R^6$, $R^7$, and $R^8$ individually represent any of hydrogen, an alkyl group having 1 to 4 carbon atoms, an alkoxy group having 1 to 4 carbon atoms, a halogen group, a haloalkyl group having 1 to 4 carbon atoms, or an aryl group having 6 to 12 carbon atoms; and
M is a central metal and represents either a Group 9 element or a Group 10 element.

3. An organometallic complex comprising a structure represented by General Formula (G3):

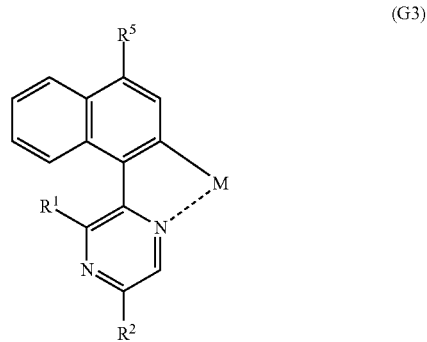

(G3)

wherein:
R¹ and R² individually represent any of an alkyl group having 1 to 4 carbon atoms, an alkoxy group having 1 to 4 carbon atoms, an alkylthio group having 1 to 4 carbon atoms, or an alkoxycarbonyl group having 1 to 5 carbon atoms;
R⁵ represents any of hydrogen, an alkyl group having 1 to 4 carbon atoms, an alkoxy group having 1 to 4 carbon atoms, a halogen group, a haloalkyl group having 1 to 4 carbon atoms, or an aryl group having 6 to 12 carbon atoms; and
M is a central metal and represents either a Group 9 element or a Group 10 element.

4. An organometallic complex represented by General Formula (G4):

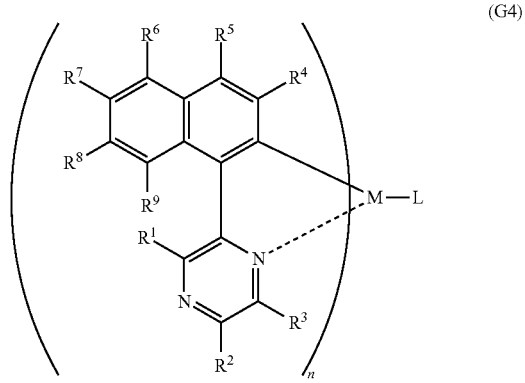

(G4)

wherein:
R¹ and R² individually represent any of an alkyl group having 1 to 4 carbon atoms, an alkoxy group having 1 to 4 carbon atoms, an alkylthio group having 1 to 4 carbon atoms, or an alkoxycarbonyl group having 1 to 5 carbon atoms;
R³ represents hydrogen or an alkyl group having 1 to 4 carbon atoms;
R⁴, R⁵, R⁶, R⁷, R⁸, and R⁹ individually represent any of hydrogen, an alkyl group having 1 to 4 carbon atoms, an alkoxy group having 1 to 4 carbon atoms, a halogen group, a haloalkyl group having 1 to 4 carbon atoms, or an aryl group having 6 to 12 carbon atoms;
M is a central metal and represents either a Group 9 element or a Group 10 element;
L represents a monoanionic ligand; and
n is 2 when the central metal is the Group 9 element or n is 1 when the central metal is the Group 10 element.

5. An organometallic complex represented by General Formula (G5):

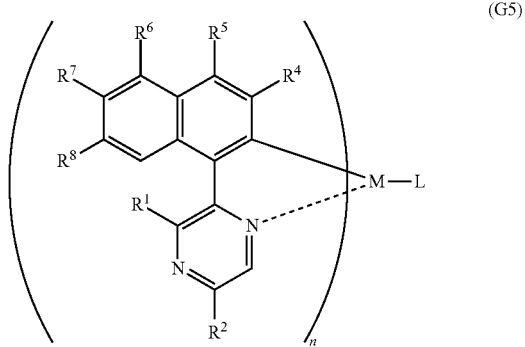

(G5)

wherein:
R¹ and R² individually represent any of an alkyl group having 1 to 4 carbon atoms, an alkoxy group having 1 to 4 carbon atoms, an alkylthio group having 1 to 4 carbon atoms, or an alkoxycarbonyl group having 1 to 5 carbon atoms;
R⁴, R⁵, R⁶, R⁷, and R⁸ individually represent any of hydrogen, an alkyl group having 1 to 4 carbon atoms, an alkoxy group having 1 to 4 carbon atoms, a halogen group, a haloalkyl group having 1 to 4 carbon atoms, or an aryl group having 6 to 12 carbon atoms;
M is a central metal and represents either a Group 9 element or a Group 10 element;
L represents a monoanionic ligand;
n is 2 when the central metal is the Group 9 element or n is 1 when the central metal is the Group 10 element.

6. An organometallic complex represented by General Formula (G6):

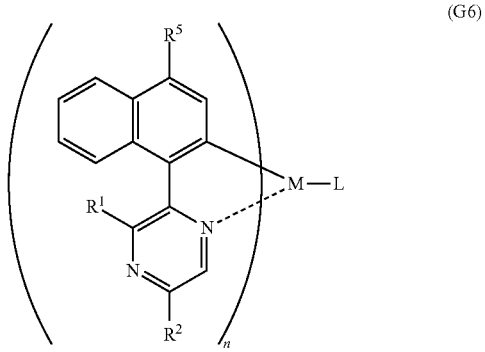

(G6)

wherein:
R¹ and R² individually represent any of an alkyl group having 1 to 4 carbon atoms, an alkoxy group having 1 to 4 carbon atoms, an alkylthio group having 1 to 4 carbon atoms, or an alkoxycarbonyl group having 1 to 5 carbon atoms;
R⁵ represents any of hydrogen, an alkyl group having 1 to 4 carbon atoms, an alkoxy group having 1 to 4 carbon atoms, a halogen group, a haloalkyl group having 1 to 4 carbon atoms, or an aryl group having 6 to 12 carbon atoms;
M is a central metal and represents either a Group 9 element or a Group 10 element;
L represents a monoanionic ligand;
n is 2 when the central metal is the Group 9 element or n is 1 when the central metal is the Group 10 element.

7. The organometallic complex according to claim 4, wherein the monoanionic ligand is any of a monoanionic bidentate chelate ligand having a beta-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen.

8. The organometallic complex according to claim 5, wherein the monoanionic ligand is any of a monoanionic bidentate chelate ligand having a beta-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen.

9. The organometallic complex according to claim 6, wherein the monoanionic ligand is any of a monoanionic bidentate chelate ligand having a beta-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen.

10. The organometallic complex according to claim 4, wherein the monoanionic ligand is represented by any of Structural Formulas (L1) to (L6)

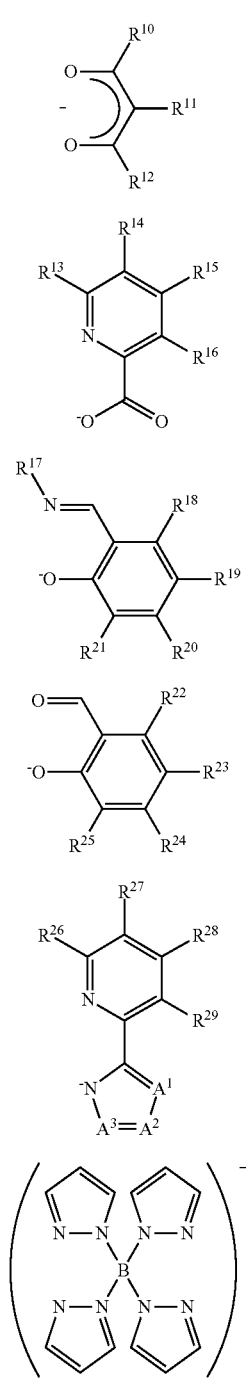

11. The organometallic complex according to claim 5, wherein the monoanionic ligand is represented by any of Structural Formulas (L1) to (L6)

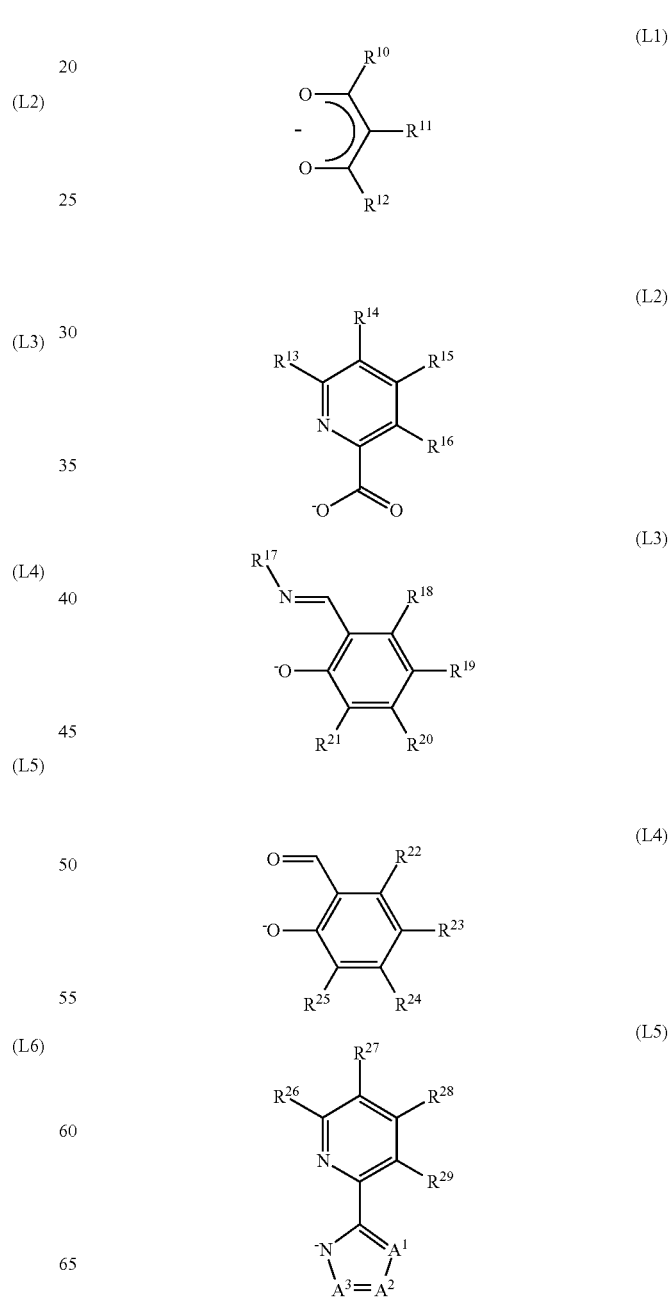

wherein:

$R^{10}$ to $R^{29}$ individually represent any of hydrogen, an alkyl group having 1 to 4 carbon atoms, a halogen group, a haloalkyl group having 1 to 4 carbon atoms, an alkoxy group having 1 to 4 carbon atoms, or an alkylthio group having 1 to 4 carbon atoms; and $A^1$, $A^2$, and $A^3$ individually represent nitrogen N or carbon C—R; and R represents any of hydrogen, an alkyl group having 1 to 4 carbon atoms, a halogen group, or a haloalkyl group having 1 to 4 carbon atoms.

-continued

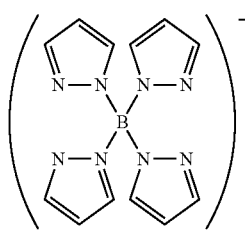
(L6)

wherein:
$R^{10}$ to $R^{29}$ individually represent any of hydrogen, an alkyl group having 1 to 4 carbon atoms, a halogen group, a haloalkyl group having 1 to 4 carbon atoms, an alkoxy group having 1 to 4 carbon atoms, or an alkylthio group having 1 to 4 carbon atoms; and $A^1$, $A^2$, and $A^3$ individually represent nitrogen N or carbon C—R; and R represents any of hydrogen, an alkyl group having 1 to 4 carbon atoms, a halogen group, or a haloalkyl group having 1 to 4 carbon atoms.

12. The organometallic complex according to claim 6, wherein the monoanionic ligand is represented by any of Structural Formulas (L1) to (L6)

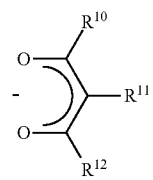
(L1)

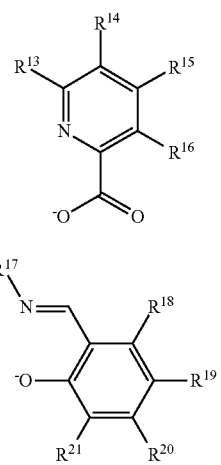
(L2)

(L3)

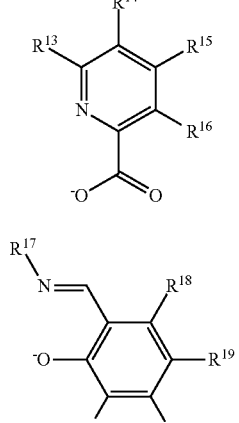

(L4)

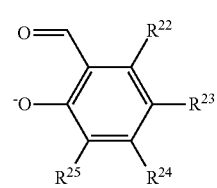

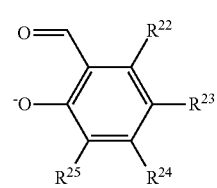

-continued

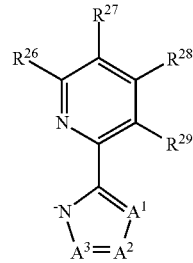
(L5)

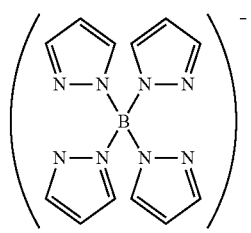
(L6)

wherein:
$R^{10}$ to $R^{29}$ individually represent any of hydrogen, an alkyl group having 1 to 4 carbon atoms, a halogen group, a haloalkyl group having 1 to 4 carbon atoms, an alkoxy group having 1 to 4 carbon atoms, or an alkylthio group having 1 to 4 carbon atoms; and $A^1$, $A^2$, and $A^3$ individually represent nitrogen N or carbon C—R; and R represents hydrogen, an alkyl group having 1 to 4 carbon atoms, a halogen group, or a haloalkyl group having 1 to 4 carbon atoms.

13. An organometallic complex represented by General Formula (G7):

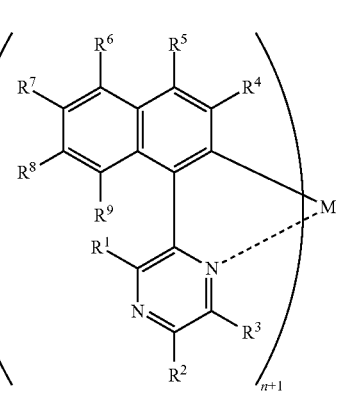
(G7)

wherein:
$R^1$ and $R^2$ individually represent any of an alkyl group having 1 to 4 carbon atoms, an alkoxy group having 1 to 4 carbon atoms, an alkylthio group having 1 to 4 carbon atoms, or an alkoxycarbonyl group having 1 to 5 carbon atoms;

$R^3$ represents hydrogen or an alkyl group having 1 to 4 carbon atoms;

$R^4$, $R^5$, $R^6$, $R^7$, $R^8$, and $R^9$ individually represent any of hydrogen, an alkyl group having 1 to 4 carbon atoms, an alkoxy group having 1 to 4 carbon atoms, a halogen group, a haloalkyl group having 1 to 4 carbon atoms, or an aryl group having 6 to 12 carbon atoms;

M is a central metal and represents either a Group 9 element or a Group 10 element; and n is 2 when the central metal is the Group 9 element or n is 1 when the central metal is the Group 10 element.

14. An organometallic complex represented by General Formula (G8):

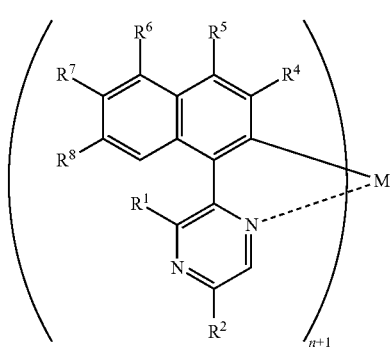

(G8)

wherein:

$R^1$ and $R^2$ individually represent any of an alkyl group having 1 to 4 carbon atoms, an alkoxy group having 1 to 4 carbon atoms, an alkylthio group having 1 to 4 carbon atoms, or an alkoxycarbonyl group having 1 to 5 carbon atoms;

$R^4$, $R^5$, $R^6$, $R^7$, and $R^8$ individually represent any of hydrogen, an alkyl group having 1 to 4 carbon atoms, an alkoxy group having 1 to 4 carbon atoms, a halogen group, a haloalkyl group, or an aryl group having 6 to 12 carbon atoms;

M is a central metal and represents either a Group 9 element or a Group 10 element; and n is 2 when the central metal is the Group 9 element or n is 1 when the central metal is the Group 10 element.

15. An organometallic complex represented by General Formula (G9):

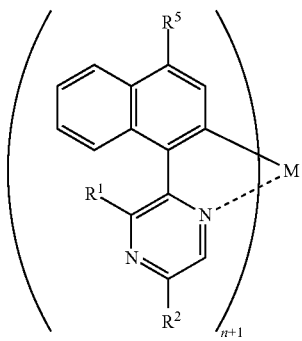

(G9)

wherein:

$R^1$ and $R^2$ individually represent any of an alkyl group having 1 to 4 carbon atoms, an alkoxy group having 1 to 4 carbon atoms, an alkylthio group having 1 to 4 carbon atoms, or an alkoxycarbonyl group having 1 to 5 carbon atoms;

$R^5$ represents any of hydrogen, an alkyl group having 1 to 4 carbon atoms, an alkoxy group having 1 to 4 carbon atoms, a halogen group, a haloalkyl group having 1 to 4 carbon atoms, or an aryl group having 6 to 12 carbon atoms;

M is a central metal and represents either a Group 9 element or a Group 10 element; and n is 2 when the central metal is the Group 9 element or n is 1 when the central metal is the Group 10 element.

16. The organometallic complex according to claim 1, wherein the central metal is iridium or platinum.

17. The organometallic complex according to claim 2, wherein the central metal is iridium or platinum.

18. The organometallic complex according to claim 3, wherein the central metal is iridium or platinum.

19. The organometallic complex according to claim 4, wherein the central metal is iridium or platinum.

20. The organometallic complex according to claim 5, wherein the central metal is iridium or platinum.

21. The organometallic complex according to claim 6, wherein the central metal is iridium or platinum.

22. The organometallic complex according to claim 13, wherein the central metal is iridium or platinum.

23. The organometallic complex according to claim 14, wherein the central metal is iridium or platinum.

24. The organometallic complex according to claim 15, wherein the central metal is iridium or platinum.

* * * * *

UNITED STATES PATENT AND TRADEMARK OFFICE
CERTIFICATE OF CORRECTION

| | | |
|---|---|---|
| PATENT NO. | : 8,399,665 B2 | Page 1 of 1 |
| APPLICATION NO. | : 12/898377 | |
| DATED | : March 19, 2013 | |
| INVENTOR(S) | : Hideko Inoue and Satoshi Seo | |

It is certified that error appears in the above-identified patent and that said Letters Patent is hereby corrected as shown below:

In the Specification:

Column 1, Line 31; Change "a photo sensitizer." to --a photosensitizer.--.
Column 6, Line 3; Change "an allylthio group" to --an alkylthio group--.
Column 17, Line 24; Change "an allylthio group" to --an alkylthio group--.
Column 17, Line 40; Change "allylthio group" to --alkylthio group--.
Column 19, Line 3; Change "a haloallyl group," to --a haloalkyl group,--.
Column 19, Line 7; Change "allyl group" to --alkyl group--.
Column 20, Line 24; Change "an allylthio group" to --an alkylthio group--.
Column 20, Line 30; Change "a haloallyl" to --a haloalkyl--.
Column 31, Line 66; Change "TDATA, M1DATA, DPAB," to --TDATA, MTDATA, DPAB,"--.
Column 33, Lines 38-39; Change "-2-yp stilbene" to -- -2-yl) stilbene--.

Signed and Sealed this
Ninth Day of July, 2013

Teresa Stanek Rea
*Acting Director of the United States Patent and Trademark Office*